United States Patent
Mistretta

(10) Patent No.: US 7,917,189 B2
(45) Date of Patent: *Mar. 29, 2011

(54) BACKPROJECTION RECONSTRUCTION METHOD FOR UNDERSAMPLED MR IMAGING

(75) Inventor: Charles A. Mistretta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1237 days.

This patent is subject to a terminal disclaimer.

(21) Appl. No.: 11/482,857

(22) Filed: Jul. 7, 2006

(65) Prior Publication Data

US 2007/0038073 A1 Feb. 15, 2007

Related U.S. Application Data

(60) Provisional application No. 60/697,607, filed on Jul. 8, 2005, provisional application No. 60/719,445, filed on Sep. 22, 2005.

(51) Int. Cl.
*A61B 5/05* (2006.01)
*G01V 3/00* (2006.01)
(52) U.S. Cl. .................................. 600/410; 324/307
(58) Field of Classification Search .................. 600/407, 600/410; 324/314; 378/4; 382/128–133
See application file for complete search history.

(56) References Cited

U.S. PATENT DOCUMENTS

| | | |
|---|---|---|
| 5,502,385 A | 3/1996 | Kuhn et al. |
| 5,603,322 A | 2/1997 | Jesmanowicz et al. |
| 5,604,778 A | 2/1997 | Polacin et al. |
| 5,933,006 A | 8/1999 | Rasche et al. |
| 6,487,435 B2 | 11/2002 | Mistretta et al. |
| 6,490,472 B1 | 12/2002 | Li et al. |
| 6,710,686 B2 | 3/2004 | Mertelmeier et al. |
| 6,807,248 B2 | 10/2004 | Mihara et al. |
| 6,954,067 B2 | 10/2005 | Mistretta |
| 2001/0027262 A1 | 10/2001 | Mistretta et al. |

FOREIGN PATENT DOCUMENTS

| | | |
|---|---|---|
| EP | 0 627 633 A1 | 7/1994 |
| WO | WO 2005/026765 | 3/2005 |
| WO | WO 2005/069031 | 7/2005 |

OTHER PUBLICATIONS

Y.Huang et al, Time-Resolved 3D MR Angiography by Interleaved Biplane Projection; Proc. Intl. Soc. Mag. Reson. Med. 13 (2005).
Wieslaw L. Nowinski, The Iterated Normalized Backprojection Method of Image Reconstruction, Institute of Computer Science, Polish Academy of Sciences Ordona 21, 01-237 Warsaw, Poland.
Y. Huang et al, Time-Rosolved 3D MR Angiography by Interleaved Biplane Projection, Proc. Intl. Soc. Mag. Reson. Med. 13 (2005).
T.A. Cashen et al, Comparison of Temporal and Spatial Undersampling Techniques for Time-Resolved Contrast-Enhanced MR Angiography, Proc. Intl. Soc. Mag. Reson. Med. 13, (2005).

(Continued)

*Primary Examiner* — Long V Le
*Assistant Examiner* — Michael T Rozanski
(74) *Attorney, Agent, or Firm* — Quarles & Brady LLP

(57) ABSTRACT

Two-dimensional or three-dimensional, time-resolved MR frame images are acquired during a dynamic study of a subject. A composite MR image is produced and this is used to reconstruct each image frame by weighting the backprojection of each projection view acquired for that image frame. The composite image may be reconstructed from views acquired separately, or it may be produced by combining views acquired during the course of the dynamic study. A number of different clinical applications of the method are described.

21 Claims, 16 Drawing Sheets

OTHER PUBLICATIONS

Graeme C. McKinnon et al, Towards Imaging the Beating Heart Usefully with a Conventional CT Scanner, Trans. on Biomedical Eng., vol. BME-28, No. 2, p. 123-127, Feb. 1981.

Kathryn L. Garden et al, 3-D Reconstruction of the Heart from few Projections: A Practical Implementation of the McKinnon-Bates Algorithm, Trans. on Biomedical Eng., vol. MI-5, No. 4, p. 233-234, Dec. 1986.

A.L. Wentland et al, Technique for Acquiring MR Image of CSF Flow During a Valsalva Maneuver, Med. Phys. Univ. of WI, Madison WI.

K.M. Johnson et al, Average and Time-Resolved Dual Velocity Encoded Phase Contrast Vastly Undersampled Isotropic Projection Imaging, Med. Phys. Univ. of WI, Madison WI.

K.M. Johnson et al, Transtenotic Pressure Gradient Measurements Using Phase Contrast Vastly Undersampled Isotropic Projection Imaging (PC-VIPR) in a Canin Model, Med. Phys. Univ. of WI. Madison WI.

C.A. Mistretta et al, Highly Constrained Backprojection for Time-Resolved MRI, Mag. Reson. Med. 55:30-40 (2006).

Zhi-Pei Liang et al, Constrained Reconstruction Methods in MR Imaging, Reviews of Mag. Reson. in Med. vol. 4, pp. 67-185, 1992.

J.G. Pipe et al, Spiral Projection Imaging: a new fast 3D trajectory, Proc. Intl. Soc. Mag. Reson. Med. 13, (2005).

K.V. Koladia et al, Rapid 3D PC-MRA using Spiral Projection Imaging, Proc. Intl. Soc. Mag. Reson. Med. 13, (2005).

J. Tsao et al, k-t Blast and k-t Sense: Dynamic MRI With High Frame Rate Exploiting. Spatiotemporal Correlations, Mag. Reson. Med. 50:1031-1042 (2003).

Zhi-Pei Liang et al, Constrained Imaging-Overcoming the Limitations of the Fourier Series, IEEE Engineering in Medicine and Biology, Sep./Oct. 1996, pp. 126-132.

Zhi-Pei Liang et al, Fast Algorithm for GS-Model-Based Image Reconstruction in Data-Sharing Fourier Imaging, IEEE Transactions on Med. Imaging, vol. 22, No. 8, pp. 1026-1030, Aug. 2003.

Klass P. Pruessmann et al, Advances in Sensitivity Encoding With Arbitrary k-Space Trajectories, Mag. Reson. in Med. 46:638-651 (2001).

R. Fahrig et al, Use of a C-Arm System to Generate True Three-dimensional Computed Rotational Angiograms: Preliminary In Vitro and In Vivo Results, AJNR: 18, pp. 1507-1514,Sep. 1997.

A.V. Barger, et al, Single Breath-Hold 3D Contrast-Enhanced Method for Assessment of Cardiac Function, Mag. Reson. in Med. 44:821-824 (2000).

J. Du et al, Time-Resolved Undersampled Projection Reconstruction Imaging for High-Resolution CE-MRA of the Distal Runoff Vessels, Mag. Reson. in Med. 48:516-522 (2002).

Ashwani Aggarwal et al, Imaging in Turbid Media by Modified Filtered Back Projection Method Using Data From Monte Carlo Simulation, Proc. of SPIE vol. 5047, pp. 314-324.

Xavier Golay, et al, Presto-Sense: An Ultrafast Whole-Brain fMRI Technique, Mag. Reson. in Med. 43:779-786 (2000).

Ronald R. Price, et al, Practical Aspects of Functional MRI (NMR Task Group #6), Medical Physics, vol. 29, No. 8, pp. 1892-1912, Aug. 2002.

M.S. Hansen et al, k-t Blast Reconstruction From Arbitrary k-t space Sampling: Application To Dynamic Radial Imaging, Proc. Intl. Soc. Mag. Reson. Med. 13 pg. 684 (2005).

Tsao J., Besinger P. and Pruessman KP, "kt-Blast and k-t Sense: Dynamic MRI with High Frame Rate Exploiting Spatiotemporal Correlations", Magn. Reson. Med. Nov. 2003; 50(5):1031-43, Hansen MS., Tsao J., Kozerke S.

Eggers H., "k-t Blast Reconstruction From Arbitrary k-t Sampling: Application to Dynamic Radial Imaging", Abstract 684, 2005 ISMRM, Miami Florida.

Pipe, Koladia, "Spiral Projection Imaging: A New Fast 3D Trajectory", Proc. Intl. Soc. Mag. Reson. Med. 13 (2005), p. 2402.

Koladia, Pipe, "Rapid 3D PC-MRA Using spiral Projection Imaging", Proc. Intl. Soc. Mag. Reson. Med. 13 (2005), p. 2403.

Huang, Gurr, Wright, "Time-Resolved 3D MR Angiography By Interleaved Biplane Projections", Proc. Intl. Soc. Mag. Reson. Med. 13 (2005), p. 1707.

Cashen, Kroeker, Leloudas, Carr, Hopkins, Carroll, "Comparison of Temporal and Spatial Undersampling Techniques for Time-Resolved Contrast-Enhanced MR Angiograpy", Proc. Intl. Soc. Mag. Reson. Med. 13 (2005), p. 380.

R. Boubertakh et al., Dynamic Images Reconstruction using kt-Blast without Training Data, Proc. Intl. Soc. Mag. Reson. Med. 11 p. 343 (2004).

P. Irarrazaval et al., Reconstruction of Undersampled Dynamic Images Based on Time Frame Registration, Proc. Intl. Soc. Mag. Reson. Med. 11 p. 342 (2004).

J. Tsao et al., Optimized canonical sampling patterns in k-t space with two and three spatial dimensions for k-t Blast and k-t', Proc. Intl. Soc. Mag. Reson. Med. 11 p. 261.

M.S. Hansen et al., A study of the spatial-temporal tradeoff in k-t Blast reconstruction, Proc. Intl. Soc. Mag. Reson. Med. 11 p. 536 (2004).

J. Tsao et al., Moving-buffer k-t Blast for real-time reconstruction: Cartesian & simplified radial cases, Proc. Intl. Soc. Mag. Reson. Med. 11 p. 635 (2004).

F. Huang et al., Reconstruction with Prior Information for Dynamic MRI, Proc. Intl. Soc. Mag. Reson. Med. 11 p. 2680 (2004).

D. Mitsouras et al., Accelerated MR Imaging via FOLDing the non-Fourier Encoded Dimensions, Proc. Intl. Soc. Mag. Reson. Med. 11 p. 2092 (2004).

P.C. Lauterbur and Z. Liang, Magnetic Resonance Imaging with a priori Constraints: Possibilities and Limitations, IEEE Engineering in Medicine and Biology Society, 1996.

C. Baltes et al., Considerations on training data in k-t Blast / k-t Sense accelerated quantitative flow measurements, Proc. Intl. Soc. Mag. Reson. Med. 13 pg. 383 (2005).

M.S. Hansen et al., On the Influence of Training Data Quality in k-t Blast Reconstruction, Mag. Reson. Med. 52:1175-1183 (2004).

M. Lustig et al., k-t Sparse: High Frame Rate Dynamic MRI Exploiting Spatio-Temporal Sparsity, Proc. Intl. Soc. Mag. Reson. Med. 14 (2006).

J. Tsao et al., Unifying Linear Prior-Information-Driven Methods for Accelerated Image Acquisition, Mag. Reson. Med. 46:652-660 (2001).

Q. Xiang and R.M. Henkelman, K-Space Description for MR Imaing of Dynamic Objects, Mag. Reson. Med. 29:422-428 (1993).

M. Lustig et al., Rapid MR Imaging with Compressed Sensing and Randomly Under-Sampled 3DFT Trajectories, Proc. Intl. Soc. Mag. Reson. Med. 14 (2006).

S. Krishnan and T.L. Chenevert, Spatio-Temporal Bandwidth-Based Acquisition for Dynamic Contrast-Enhanced Magnetic Resonance Imaging, J. Mag. Reson. Imaging 20:129-137 (2004).

M.S. Hansen et al., k-t Blast Reconstruction From Non-Cartesian k-t Space Sampling, Mag. Reson. Med. 55:85-91 (2006).

A.G. Webb et al., Application of Reduced-Encoding MR Imaging with Generalized-Series Reconstruction (RIGR), J. Mag. Reson. Imaging 3:925-928 (1993).

B. Madore and N.J. Pelc, New Approach to 3D Time-Resolved Angiography, Mag. Reson. Med. 47:1022-1025 (2002).

J. Tsao et al., Optimizing Spatiotemporal Sampling for k-t Blast and k-t Sense: Application to High-Resolution Real-Time Cardiac Steady-State Free Precession, Mag. Reson. Med. 53:1372-1382 (2005).

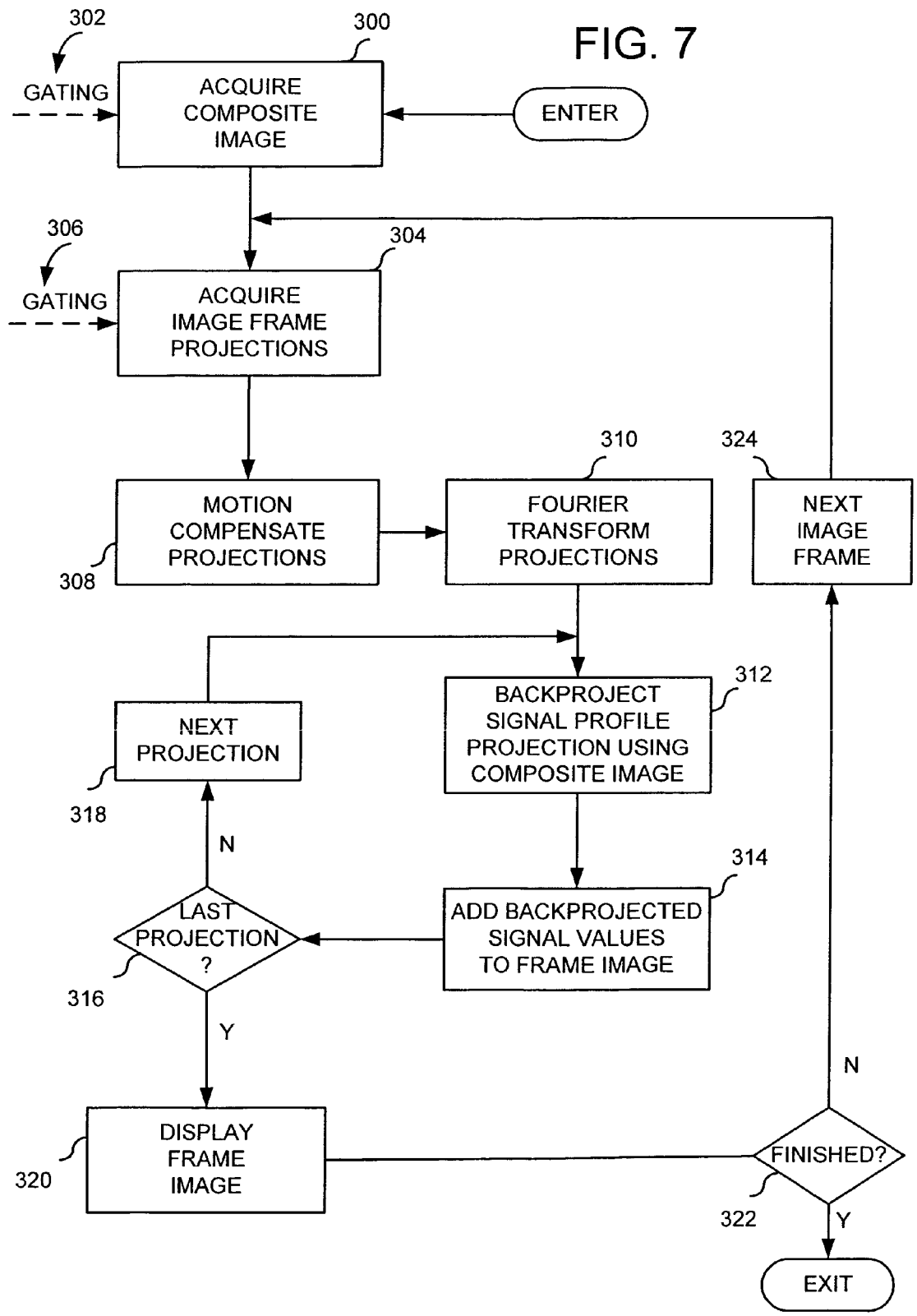

FIG. 9
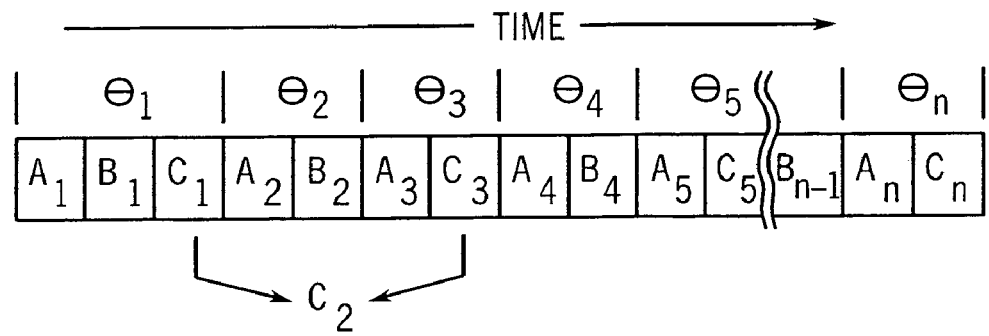
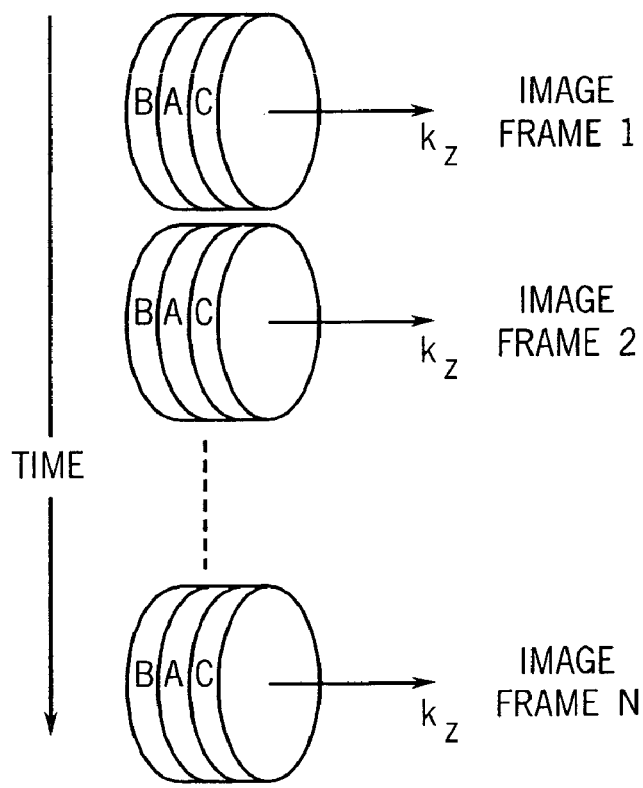
FIG. 10

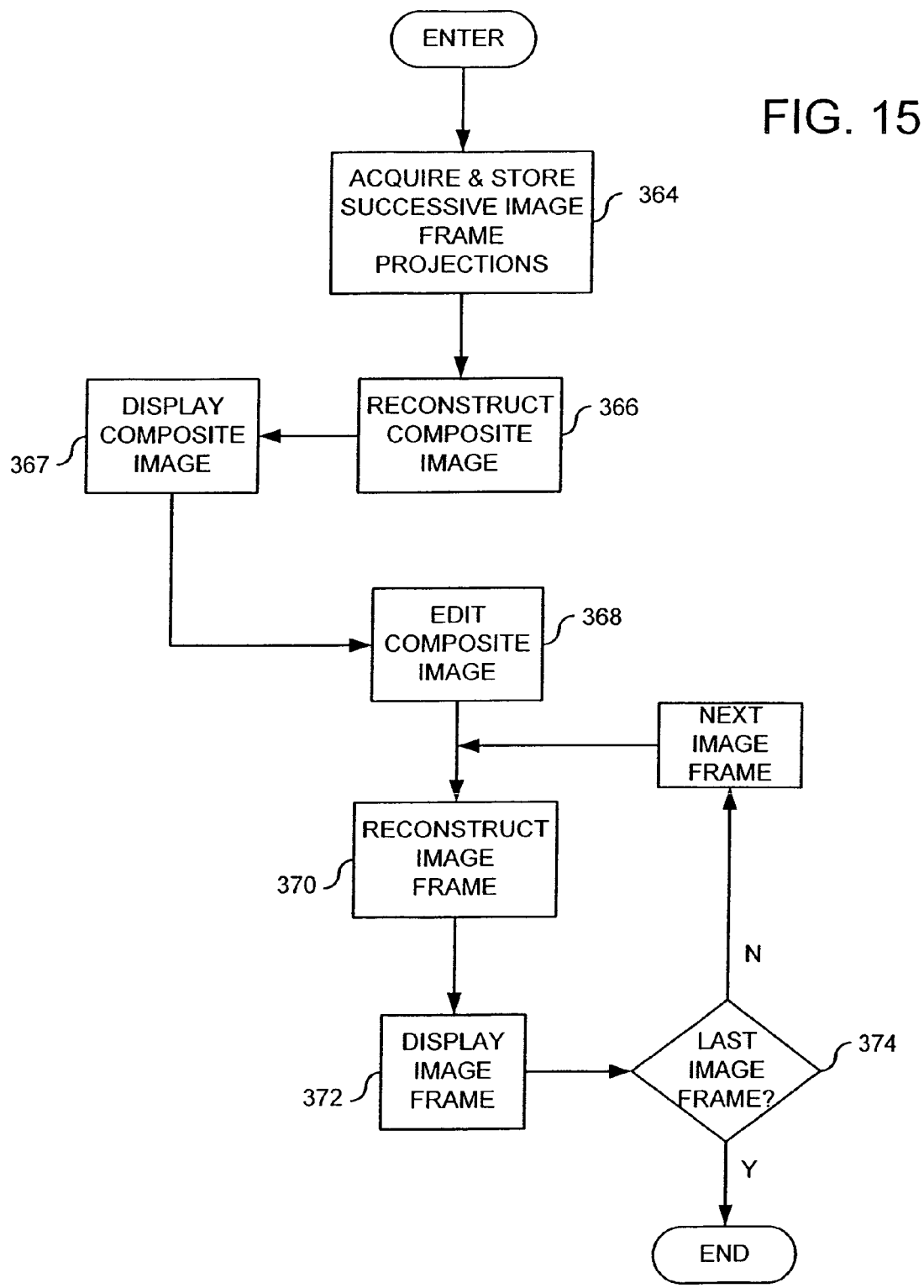

BACKPROJECTION RECONSTRUCTION METHOD FOR UNDERSAMPLED MR IMAGING

CROSS-REFERENCE TO RELATED APPLICATIONS

This application claims the benefit of U.S. Provisional patent application Ser. No. 60/697,607 filed on Jul. 8, 2005 and entitled "Backprojection Reconstruction Method For Undersampled Time-Resolved MR Imaging;" and U.S. Provisional patent application Ser. No. 60/719,445, filed on Sep. 22, 2005 and entitled "Highly Constrained Image Reconstruction Method".

STATEMENT REGARDING FEDERALLY SPONSORED RESEARCH

This invention was made with government support under Grant No. 1R01HL72260-01 awarded by the National Institute of Health. The United States Government has certain rights in this invention.

BACKGROUND OF THE INVENTION

The field of the invention is magnetic resonance imaging ("MRI"), and particularly, the reconstruction of MR images.

Magnetic resonance imaging uses the nuclear magnetic resonance (NMR) phenomenon to produce images. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins, and after the excitation signal $B_1$ is terminated, this signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. Each measurement is referred to in the art as a "view" and the number of views determines the resolution of the image. The resulting set of received NMR signals, or views, or k-space samples, are digitized and processed to reconstruct the image using one of many well known reconstruction techniques. The total scan time is determined in part by the number of measurement cycles, or views, that are acquired for an image, and therefore, scan time can be reduced at the expense of image resolution or image signal-to-noise ratio ("SNR") by reducing the number of acquired views.

The most prevalent method for acquiring an NMR data set from which an image can be reconstructed is referred to as the "Fourier transform" imaging technique or "spin-warp" technique. This technique is discussed in an article entitled "Spin-Warp NMR Imaging and Applications to Human Whole-Body Imaging", by W. A. Edelstein et al., *Physics in Medicine and Biology*, Vol. 25, p. 751-756 (1980). It employs a variable amplitude phase encoding magnetic field gradient pulse prior to the acquisition of NMR signals to phase encode spatial information in the direction of this gradient. In a two-dimensional implementation (2DFT), for example, spatial information is encoded in one direction by applying a phase encoding gradient ($G_y$) along that direction, and then a signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($G_{y_i}$) in the sequence of views that are acquired during the scan. In a three-dimensional implementation (3DFT) a third gradient ($G_z$) is applied before each signal readout to phase encode along the third axis. The magnitude of this second phase encoding gradient pulse $G_z$ is also stepped through values during the scan. These 2DFT and 3DFT methods sample k-space in a rectilinear pattern such as that shown in FIG. 2A and they require considerable scan time in order to sample k-space adequately.

There has been extensive recent work using multiple receiver coil arrays to shorten imaging scan time. In the SMASH technique described by Griswold, et al., "Simultaneous Acquisition Of Spatial Harmonics (SMASH)" *Magnetic Resonance In Medicine* 1999, June; 41(6):1235-45, multiple coils are carefully positioned in one of the Fourier phase encoding directions. Using knowledge of the coil sensitivities non-acquired phase encodings can be synthesized, thus increasing the rate at which images of a given resolution can be acquired, or increasing the resolution of images acquired at the same rate. The SENSE technique described by Pruessmann et al., "Coil Sensitivity Encoding For Fast MRI", MRM 42:952-962 (1999) is another such multiple receive channel approach to reducing scan time. The SMASH and SENSE methods are characterized by a factor "R" representing the speed increase over conventional methods on the order of 2 to 3 for a given resolution. They are also characterized by a factor "g", on the order of 1-1.2 representing the increase in noise beyond what would be expected for a given imaging time.

There has also been recent work using projection reconstruction methods for acquiring MRI data as disclosed in U.S. Pat. No. 6,487,435. Projection reconstruction methods have been known since the inception of magnetic resonance imaging. Rather than sampling k-space in a rectilinear scan pattern as is done in Fourier imaging and shown in FIG. 2A, projection reconstruction methods sample k-space with a series of views that sample radial lines extending outward from the center of k-space as shown in FIG. 2B. The number of views needed to sample k-space determines the length of the scan and if an insufficient number of views are acquired, streak artifacts are produced in the reconstructed image. The technique disclosed in U.S. Pat. No. 6,487,435 reduces such streaking by acquiring successive undersampled images with interleaved views and sharing peripheral k-space data between successive images. This method of sharing acquired peripheral k-space data is known in the art by the acronym "TRICKS".

There are two methods used to reconstruct images from an acquired set of k-space projection views as described, for example, in U.S. Pat. No. 6,710,686. The most common method is to regrid the k-space samples from their locations on the radial sampling trajectories to a Cartesian grid. The image is then reconstructed by performing a 2D or 3D Fourier transformation of the regridded k-space samples in the conventional manner.

The second method for reconstructing an image is to transform the radial k-space projection views to Radon space by Fourier transforming each projection view. An image is reconstructed from these signal projections by filtering and backprojecting them into the field of view (FOV). As is well known in the art, if the acquired signal projections are insufficient in number to satisfy the Nyquist sampling theorem, streak artifacts will be produced in the reconstructed image.

The standard backprojection method is illustrated in FIG. 3. Each Radon space signal projection profile 11 is backprojected onto the field of view 13 by projecting each signal sample 15 in the profile 11 through the FOV 13 along the projection path as indicted by arrows 17. In projecting each signal sample 15 in the FOV 13 we have no a priori knowledge of the subject and the assumption is made that the NMR signals in the FOV 13 are homogeneous and that the signal sample 15 should be distributed equally in each pixel through which the projection path passes. For example, a projection path 8 is illustrated in FIG. 3 for a single signal sample 15 in one signal projection profile 11 as it passes through N pixels in the FOV 13. The signal value (P) of this signal sample 15 is divided up equally between these N pixels in a conventional backprojection:

$$S_n = (P \times 1)/N \quad (1)$$

where: $S_n$ is the NMR signal value distributed to the $n^{th}$ pixel in a projection path having N pixels through the FOV 13.

Clearly, the assumption that the NMR signal in the FOV 13 is homogeneous is not correct. However, as is well known in the art, if certain corrections are made to each signal profile 11 and a sufficient number of profiles are acquired at a corresponding number of projection angles, the errors caused by this faulty assumption are minimized and image artifacts are suppressed. In a typical, filtered backprojection method of image reconstruction, 400 projections are required for a 256× 256 pixel 2D image and 203,000 projections are required for a 256×256 ×256 pixel 3D image. If the method described in the above-cited U.S. Pat. No. 6,487,435 is employed, the number of projection views needed for these same images can be reduced to 100 (2D) and 2000 (3D).

The kt-blast technique disclosed by Tsao J., Besinger P. and Pruessman KP, "kt-Blast and k-t Sense: Dynamic MRI with High Frame Rate Exploiting Spatiotemporal Correlations", Magn. Reson. Med. 2003 November; 50(5):1031-43, Hansen MS., Tsao J., Kozerke S., and Eggers H., "k-t Blast Reconstruction From Arbitrary k-t Sampling: Application to Dynamic Radial Imaging", Abstract 684, 2005 ISMRM, Miami Fla., recognizes that in an acquired time series there is a great deal of correlation in the k-space data associated with an acquired set of time frames. In kt-blast, which has been applied to radial acquisitions, a low spatial frequency training data set is acquired to remove the aliasing that occurs when undersampling is performed in the spatial and temporal domains. Using iterative image reconstruction, significant reductions in the required data can be achieved.

An angiographic technique that also incorporates the idea of using a training data set to guide the reconstruction of images using pairs of orthogonal 2D projection images has been described by Huang Y., Gurr D., and Wright G., "Time-Resolved 3D MR Angiography By Interleaved Biplane Projections", Abstract 1707, ISMRM 2005, Miami Fla. In this method an iterative image reconstruction is guided using correlation analysis of data from a training data set that is comprised of all acquired orthogonal 2D projection images.

SUMMARY OF THE INVENTION

The present invention is a new method for reconstructing magnetic resonance images, and particularly, an improved backprojection method. A composite image is acquired as part of the MRI scan, and it is reconstructed to provide a priori knowledge of the subject being imaged. This composite image is used during the reconstruction of highly under sampled image frames to weight the distribution of backprojected views in each image frame. As a result, far fewer projection views need be acquired resulting in a much shorter scan time. A speed increase factor (R) from 10 to 100 is possible depending on the details of the image.

A discovery of the present invention is that good quality images can be produced with far fewer projection signal profiles if a priori knowledge of the signal contour in the FOV is used in the reconstruction process. Referring to FIG. 4, for example, the signal contour in the FOV 13 may be known to include structures such as blood vessels 19 and 21. That being the case, when the backprojection path 8 passes through these structures a more accurate distribution of the signal sample 15 in each pixel is achieved by weighting the distribution as a function of the known signal contour at that pixel location. With such weighting, a majority of the signal sample 15 will be distributed in the example of FIG. 4 at the pixels that intersect the known structures 19 and 21. For a backprojection path 8 having N pixels this highly constrained backprojection may be expressed as follows:

$$S_n = (P \times C_n) \Big/ \sum_{n=1}^{N} C_n \quad (2)$$

where: $S_n$=the backprojected signal magnitude at a pixel n in an image frame being reconstructed;

P=the signal sample value in the projection profile being backprojected; and $C_n$=signal value of an a priori composite image at the $n^{th}$ pixel along the backprojection path. The composite image is reconstructed from data acquired during the scan, and may include that used to reconstruct the image frame as well as other acquired image data that depicts the structure in the field of view. The numerator in equation (2) weights each pixel using the corresponding signal value in the composite image and the denominator normalizes the value so that all backprojected signal samples reflect the projection sums for the image frame and are not multiplied by the sum of the composite image. It should be noted that while the normalization can be performed on each pixel separately after the backprojection is performed, in many clinical applications it is far easier to normalize the projection P before the backprojection. In this case, the projection P is normalized by dividing by the corresponding value $P_c$ in a projection through the composite image at the same view angle. The normalized projection $P/P_c$ is then backprojected and the resulting image is then multiplied by the composite image.

A 3D embodiment of the highly constrained backprojection is shown pictorially in FIG. 5 for a single 3D projection view characterized by the view angles θ and φ. This projection view is back projected along axis 17 and spread into a Radon plane 25 at a distance r along the back projection axis 17. Instead of a filtered back projection in which projection signal values are filtered and uniformly distributed into the successive Radon planes, along axis 17, the projection signal values are distributed in the Radon plane 25 using the information in the composite image. The composite image in the example of FIG. 5 contains vessels 19 and 21. The weighted signal contour value is deposited at image location x, y, z in the Radon plane 25 based on the intensity at the corresponding location x, y, z in the composite image. This is a simple multiplication of the backprojected signal profile value P by the corresponding composite image voxel value. This product is then normalized by dividing the product by the projection profile value from the corresponding image space projection profile formed from the composite image. The formula for the 3D highly constrained reconstruction is $$I(x, y, z) = \sum (P(r, \theta, \phi) * C(x, y, z)_{(r,\theta,\phi)} / P_c(r, \theta, \phi)) \quad (2a)$$

where the sum ($\Sigma$) is over all projections in the image frame being reconstructed and the x, y, z values in a particular Radon plane are calculated using the projection profile value $P(r,\theta,\phi)$ at the appropriate $r,\theta,\phi$ value for that plane. $P_c(r,\theta,\phi)$ is the corresponding projection profile value from the composite image, and $C(x,y,z)_{r,\theta,\phi}$ is the composite image value at $(r,\theta,\phi)$.

Another discovery of the present invention is that there are a number of clinical MR applications in which a priori information is available and a composite image can be reconstructed and used to enhance the reconstruction of undersampled images. When a series of time-resolved images are acquired in a dynamic study, each image frame may be reconstructed using a very limited set of acquired views. However, each such set of views is interleaved with the views acquired for other image frames, and after a number of image frames have been acquired, a sufficient number of different views are available to reconstruct a quality composite image for use according to the present invention.

Another aspect of the present invention is the application of the highly constrained image reconstruction method to contrast enhanced magnetic resonance angiography ("CEMRA"). With CEMRA, images of subject vasculature are acquired both before and after administration of a contrast agent. The former image serves as a mask which is subtracted from the contrast enhanced image to remove all stationary tissues from the final angiogram. With the image reconstruction method of the present invention the mask can be subtracted in additional ways to enhance its effectiveness. First, the mask image can be subtracted from the composite image before it is used to reconstruct the final image. Or, each k-space projection in the acquired image data set may have the corresponding k-space projection in the mask data set subtracted from it prior to its highly constrained backprojection. Or, both of the above mask subtraction methods can be used during the same reconstruction.

Another aspect of the present invention is the application of the highly constrained image reconstruction method to a dynamic study in which a series of image frames are acquired. During such dynamic studies the subject changes and a single composite image may not accurately depict the subject throughout the entire study. For example, CEMRA image frames may be acquired as the contrast agent flows into the vasculature of interest. In order to better see the changes that occur during the study, more than one composite image is used to reconstruct the image frames. More specifically, the composite image used to reconstruct an image frame is formed from the projection views used to reconstruct the image frame itself plus the interleaved projection views acquired in a surrounding time window. The narrower the time window, the more accurately the composite image will reflect the changing subject at the moment the image frame is acquired.

Yet another aspect of the present invention is the application of the highly constrained image reconstruction method to a dynamic study in which a series of image frames are acquired and reconstructed using the TRICKS view sharing method. In this application a separate composite image may be produced for the central region of k-space and each of the peripheral segments of k-space for use during the image reconstruction, or a single composite image may be reconstructed for all the regions.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 7 is a flow chart of a first preferred method for employing the present invention in an MR imaging application;

FIG. 9 is a pictorial representation of the k-space sampling sequence used in the TRICKS embodiment of FIGS. 8A and 8B;

FIG. 10 is a pictorial representation of the k-space data sets produced with the TRICKS embodiment of FIGS. 8A and 8B;

FIG. 15 is a flow chart of a variation that can be used to remove unwanted objects from the FOV being imaged.

DETAILED DESCRIPTION OF THE PREFERRED EMBODIMENT

Figure 1:
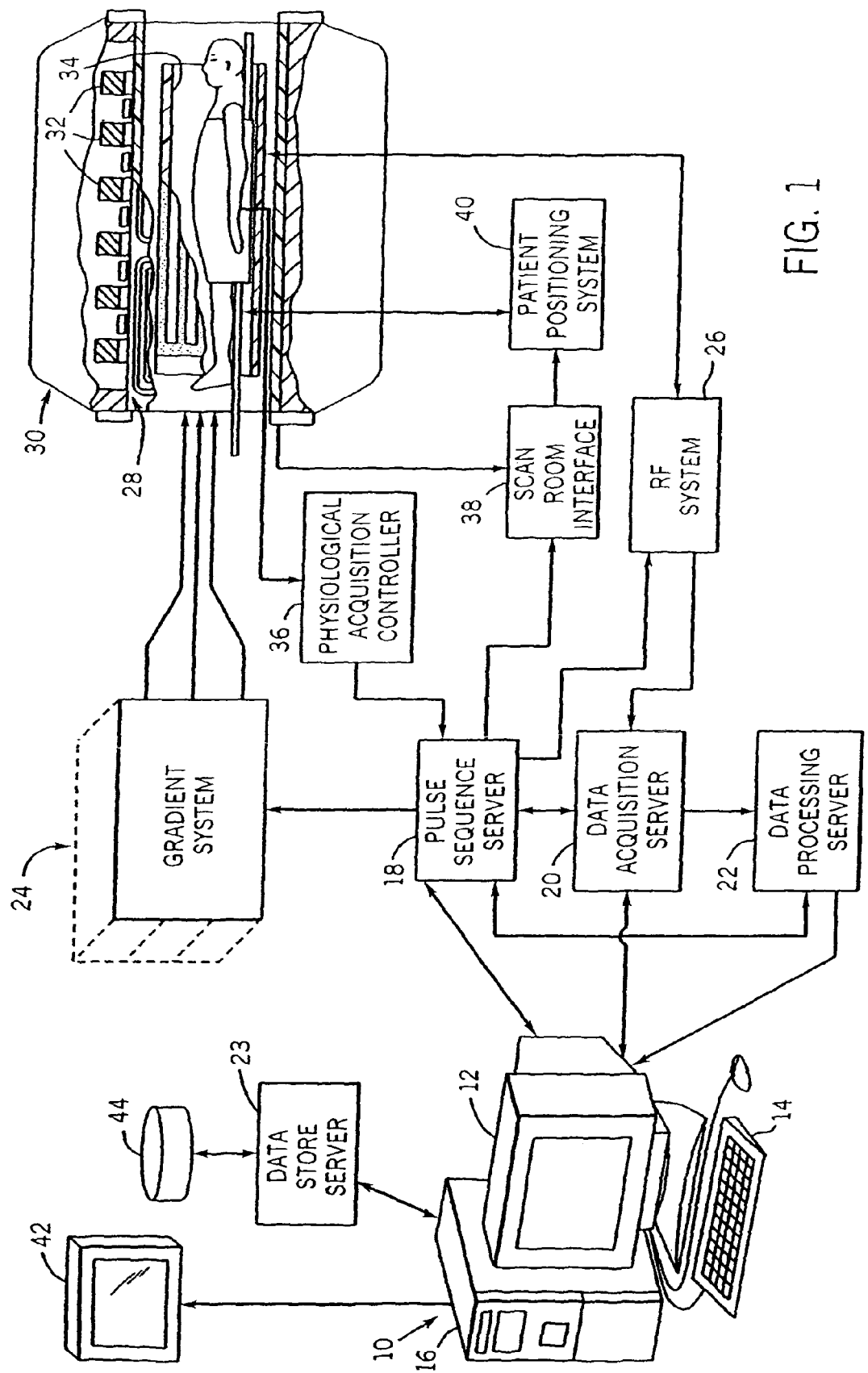
FIG. 1 is a block diagram of an MRI system which employs the present invention.
Figure 2A:
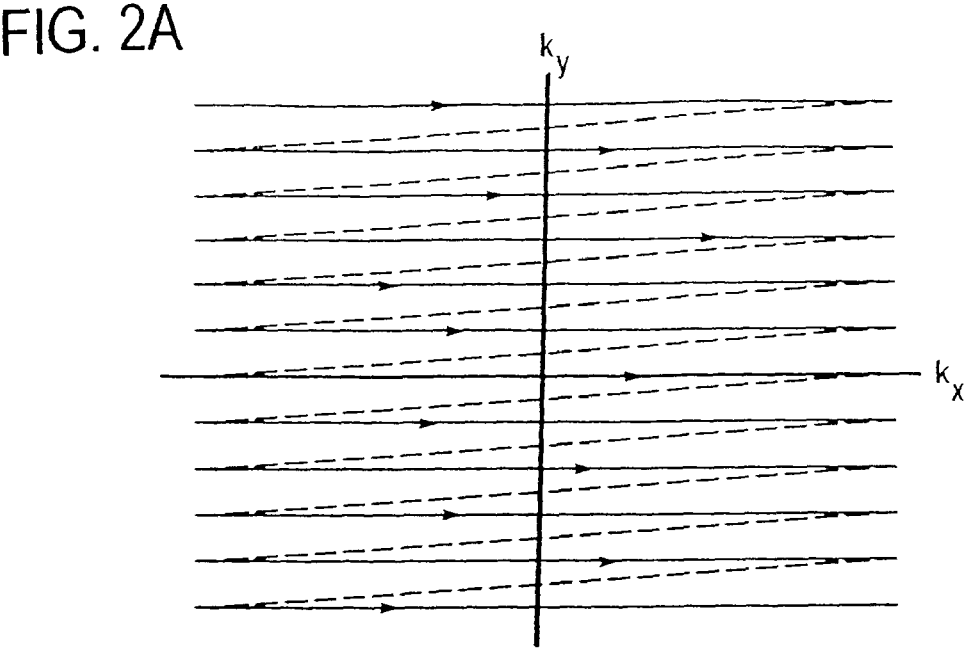
FIG. 2A is a graphic illustration of the manner in which k-space is sampled during a typical Fourier, or spin-warp, image acquisition using the MRI system of FIG. 1.
Figure 2B:
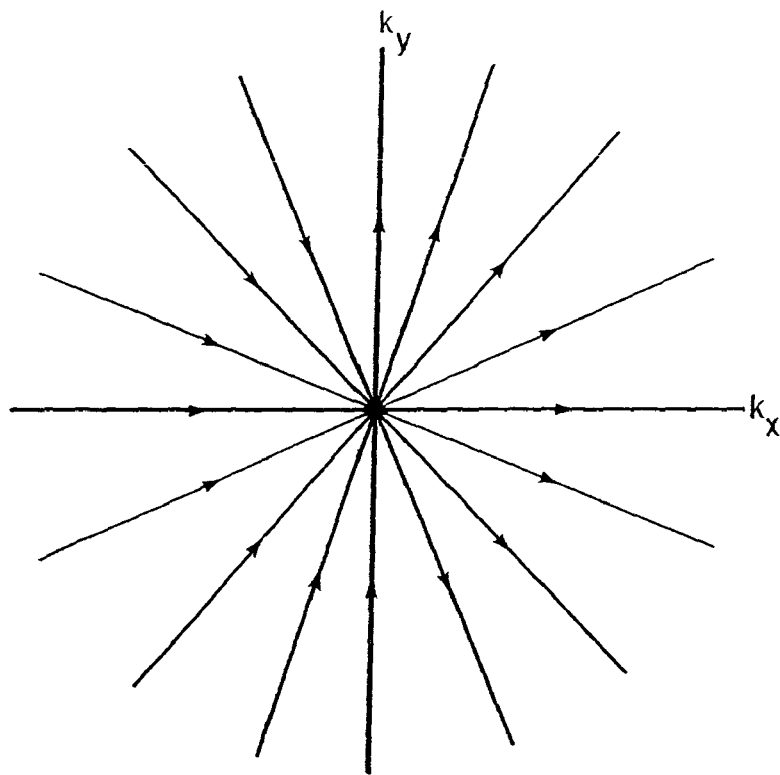
FIG. 2B is a graphic illustration of the manner in which k-space is sampled during a typical projection reconstruction image acquisition.
Figure 3:
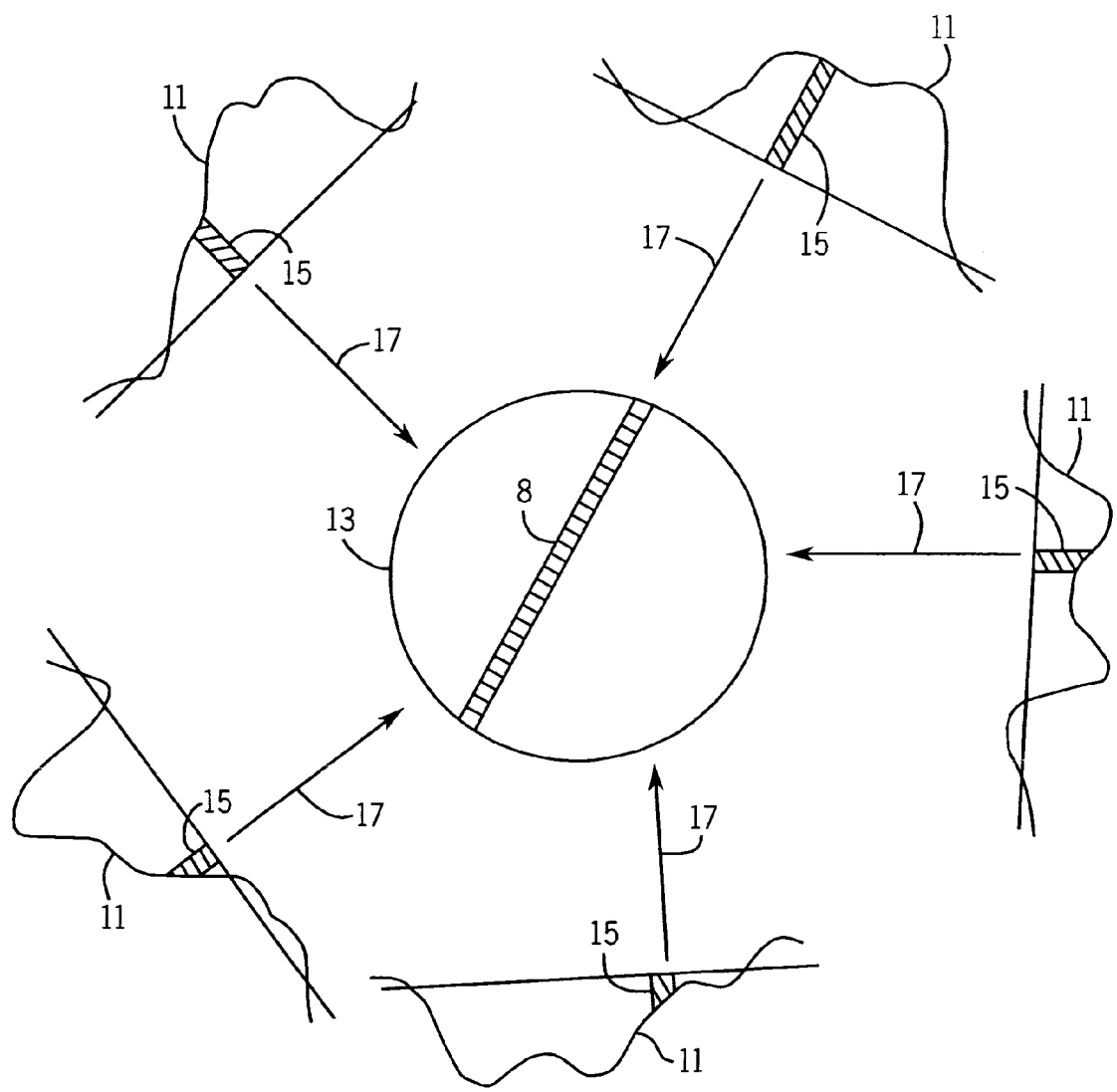
FIG. 3 is a pictorial representation of a conventional backprojection step in an image reconstruction process.

Referring particularly to FIG. 1, a preferred embodiment of the invention is employed in an MRI system. The MRI system includes a workstation 110 having a display 112 and a keyboard 114. The workstation 110 includes a processor 116 which is a commercially available programmable machine running a commercially available operating system. The workstation 110 provides the operator interface which enables scan prescriptions to be entered into the MRI system.

The workstation 110 is coupled to four servers: a pulse sequence server 118; a data acquisition server 120; a data processing server 122, and a data store server 23. In the preferred embodiment the data store server 123 is performed by the workstation processor 116 and associated disc drive interface circuitry. The remaining three servers 118, 120 and 122 are performed by separate processors mounted in a single enclosure and interconnected using a 64-bit backplane bus. The pulse sequence server 118 employs a commercially available microprocessor and a commercially available quad communication controller. The data acquisition server 120 and data processing server 122 both employ the same commercially available microprocessor and the data processing server 122 further includes one or more array processors based on commercially available parallel vector processors.

The workstation 110 and each processor for the servers 18, 20 and 22 are connected to a serial communications network. This serial network conveys data that is downloaded to the servers 118, 120 and 122 from the workstation 110 and it conveys tag data that is communicated between the servers and between the workstation and the servers. In addition, a high speed data link is provided between the data processing server 122 and the workstation 110 in order to convey image data to the data store server 123.

The pulse sequence server 118 functions in response to program elements downloaded from the workstation 110 to operate a gradient system 124 and an RF system 126. Gradient waveforms necessary to perform the prescribed scan are produced and applied to the gradient system 124 which excites gradient coils in an assembly 128 to produce the magnetic field gradients Gx, Gy and Gz used for position encoding NMR signals. The gradient coil assembly 128 forms part of a magnet assembly 130 which includes a polarizing magnet 132 and a whole-body RF coil 134.

RF excitation waveforms are applied to the RF coil 134 by the RF system 126 to perform the prescribed magnetic resonance pulse sequence. Responsive NMR signals detected by the RF coil 134 are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays.

The RF system 126 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M = \sqrt{I^2 + Q^2}$$

and the phase of the received NMR signal may also be determined:

$$\varphi = \tan^{-1} Q/I.$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 which receives signals from various sensors associated with the condition of the patient and the magnet system. It is also through the scan room interface circuit 138 that a patient positioning system 140 receives commands to move the patient to desired positions during the scan.

It should be apparent that the pulse sequence server 118 performs real-time control of MRI system elements during a scan. As a result, it is necessary that its hardware elements be operated with program instructions that are executed in a timely manner by run-time programs. The description components for a scan prescription are downloaded from the workstation 110 in the form of objects. The pulse sequence server 118 contains programs which receive these objects and converts them to objects that are employed by the run-time programs.

The digitized NMR signal samples produced by the RF system 126 are received by the data acquisition server 120. The data acquisition server 120 operates in response to description components downloaded from the workstation 110 to receive the real-time NMR data and provide buffer storage such that no data is lost by data overrun. In some scans the data acquisition server 120 does little more than pass the acquired NMR data to the data processor server 122. However, in scans which require information derived from acquired NMR data to control the further performance of the scan, the data acquisition server 120 is programmed to produce such information and convey it to the pulse sequence server 118. For example, during prescans NMR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process NMR signals used to detect the arrival of contrast agent in an MRA scan. In all these examples the data acquisition server 120 acquires NMR data and processes it in real-time to produce information which is used to control the scan.

The data processing server 122 receives NMR data from the data acquisition server 120 and processes it in accordance with description components downloaded from the workstation 110. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc. As will be described in more detail below, the present invention is implemented by the MRI system in response to a program executed by the data processing server 122.

Images reconstructed by the data processing server 122 are conveyed back to the workstation 110 where they are stored. Real-time images are stored in a data base memory cache (not shown) from which they may be output to operator display 112 or a display 142 which is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

To practice some of the preferred embodiments of the invention NMR data is acquired in a 3D spherical k-space coordinate system, with the readout gradient direction defined by the angle θ from the $k_z$-axis and by the angle φ from the $k_y$-axis. The sampling method consists of a series of equally spaced projections with all projections going through the center of k-space. The maximum k-space radius value ($k_{max}$) determines the resolution in all three spatial directions of the resulting image. The radial sample spacing ($\Delta k_r$) determines the diameter (D) of the full field of view (FOV) of the reconstructed image. The full FOV image may be reconstructed without artifacts if the Nyquist condition is met, Δk, $\Delta k \leq \Delta k_r$. If this condition is not satisfied, however, alias-free reconstruction still occurs within a reduced diameter (d) that is less than the full FOV (D). If it is assumed that the projections are acquired evenly spaced ($\Delta k = \Delta k = \Delta k_r$), then the surface area A at $k_{max}$ associated with a projection is $$A = \Delta k^2 = \frac{2\pi}{N_p} k_{max}^2 \quad (3)$$

where $N_p$ is the number of acquired views, or projections. Equation (3) determines Δk, by which the diameter (d) of the reduced FOV due to the angular spacing of the projection views can be related to the full FOV diameter D as follows:

$$\frac{d}{D} = \frac{2}{N_R}\sqrt{\frac{N_P}{2\pi}}$$

where $N_R$ is the matrix size (i.e. number of samples during the signal readout) across the FOV. In the image domain, a well-constructed reduced FOV appears centered around each object even if the Nyquist condition is not met. However, radial streak artifacts from outside can enter the local FOV. The condition that k-space be fully sampled, or d=D, requires that the number of sampled projections be:

$$N_P = \frac{\pi}{2} N_R^2. \quad (4)$$

If $N_R$=256 samples are acquired during the readout of each acquired NMR signal, for example, the number of projections $N_p$ required to meet the Nyquist condition is around 103,000.

A pulse sequence used to acquire data as 3D projections is shown in FIG. 6. The sequence is implemented on the above described MRI system equipped with a high-performance gradient subsystem (40 mT/m maximum amplitude and 150 T/m/sec maximum slew rate). Either full-echo or partial-echo readouts can be performed during a data acquisition window 200. If partial echo is chosen, the bottom half of k-space ($k_z$<0) is only partially acquired. Because of the large FOV in all directions, a non-selective radio-frequency (RF) pulse 202 can be used to produce transverse magnetization throughout the image FOV.

A gradient-recalled NMR echo signal 203 is produced by spins in the excited FOV and acquired in the presence of three readout gradients 206, 208 and 210. Since a slab-select gradient is not required, the readout gradient waveforms $G_x$, $G_y$, and $G_z$ have a similar form. This symmetry is interrupted only by the need to spoil the sequence, which is accomplished by playing a dephasing gradient lobe 204. The $G_x$ and $G_y$ readout gradients 208 and 210 are rewound by respective gradient pulses 212 and 214 to achieve steady state.

The readout gradient waveforms $G_x$, $G_y$ and $G_z$ are modulated during the scan to sample radial trajectories at different angles. The angular spacing is chosen such that a uniform distribution of k-space sample points occurs at the peripheral boundary ($k_{max}$) of the sampled k-space sphere. Although several methods of calculating the distribution are known, a method which evenly distributes the projections by sampling the spherical surface with a spiral trajectory, with the conditions of constant path velocity and surface area coverage is used. This solution also has the benefit of generating a continuous sample path, which reduces gradient switching and eddy currents. For N total projections, the equations for the gradient amplitude as a function of projection number n are:

$$G_z = \frac{2n-1}{2N} \quad (5)$$

$$G_x = \cos(\sqrt{2N\pi}\sin^{-1}G_z(n))\sqrt{1-G_z(n)^2} \quad (6)$$

$$G_y = \cos(\sqrt{2N\pi}\sin^{-1}G_z(n))\sqrt{1-G_z(n)^2}. \quad (7)$$

If a fully sampled image acquisition is to be performed, N is set to $N_p$ as defined above in equation (4) and a series of N=$N_p$ pulse sequences are performed. The readout gradient amplitudes for the $n^{th}$ pulse sequence in this series is given by equations (5), (6) and (7). While n can be indexed from 1 to N in monotonic order during the scan, it can be appreciated that other orders are possible. As will be described below, the present invention enables the spherical k-space to be sampled with far fewer projection views, which results in a shorter scan time.

Figure 6A:
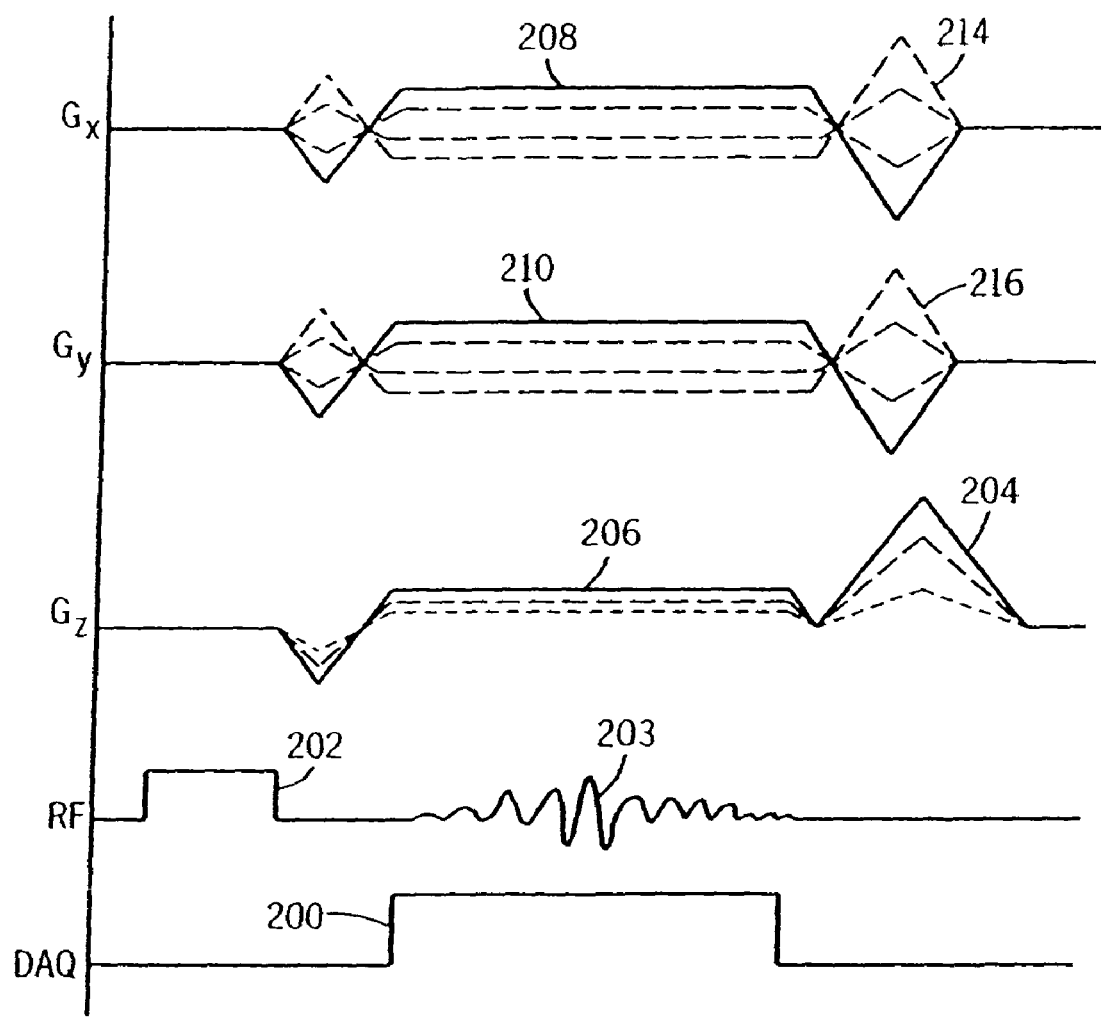
FIG. 6A is a graphic illustration of a preferred pulse sequence for directing the MRI system of FIG. 1 to acquire a 3D projection reconstruction image.
Figure 6B:
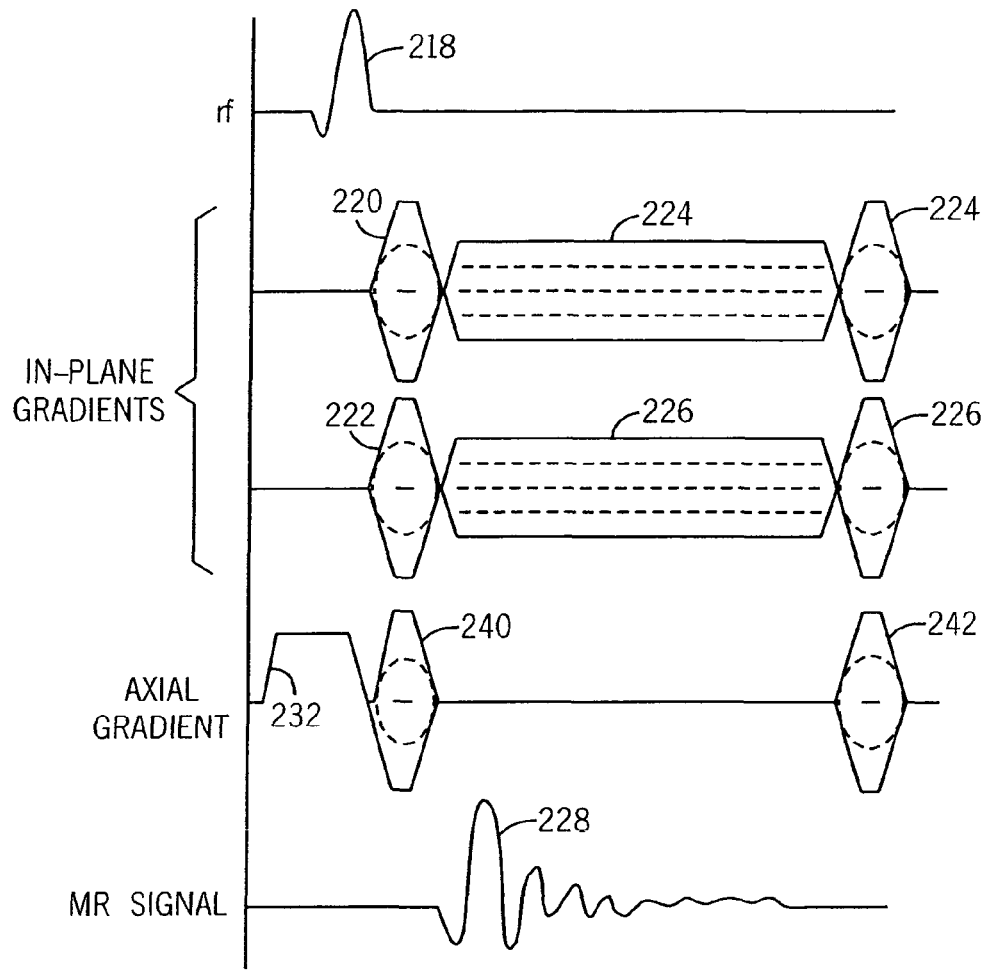
FIG. 6B is a graphic illustration of another preferred pulse sequence for use in practicing the present invention.

Another pulse sequence used to practice a number of embodiments of the present invention is shown in FIG. 6B. This is a fast gradient-recalled echo pulse sequence in which a selective, asymmetrically truncated sinc rf excitation pulse 218 is produced in the presence of a slab-select gradient 232. The flip angle of the rf pulse 218 is set near the Ernst angle for $T_1$ shortened blood which is typically 30° to 40°.

Figure 6C:
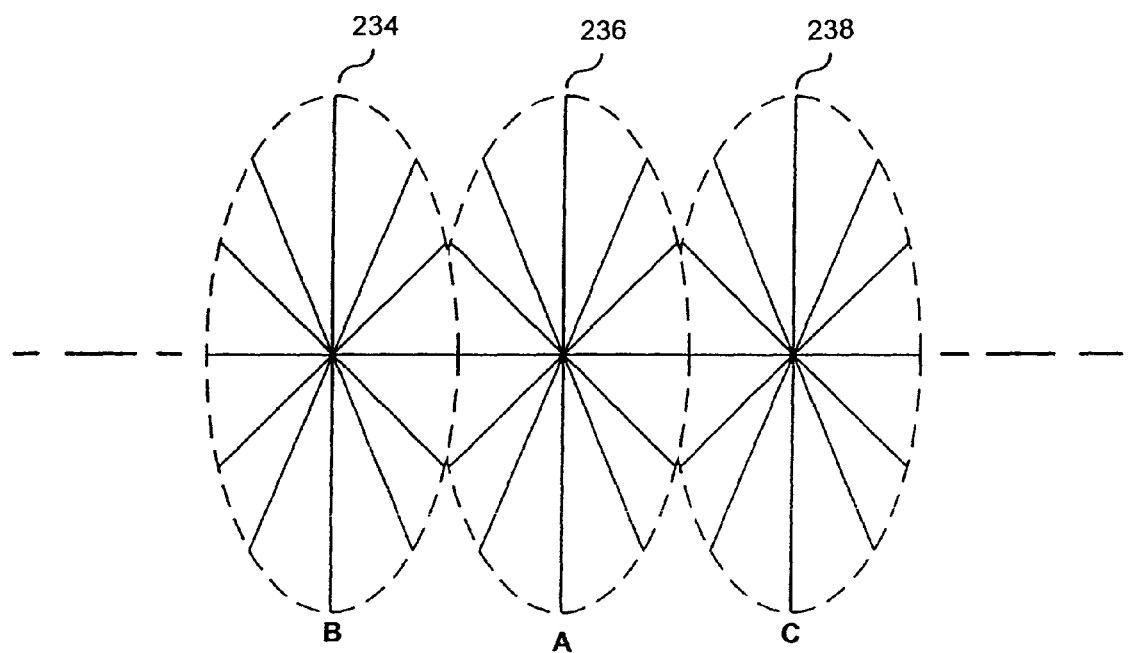
FIG. 6C is a pictorial representation of the k-space sampling pattern performed with the pulse sequence of FIG. 6B.

This pulse sequence may be used to acquire a single 2D slice by sampling in a single k-space circular slice, or it may be used to sample a plurality of circular k-space slices as shown at 234, 236 and 238 in FIG. 6C. When multiple 2D slices are acquired the axial gradient produces the slab select gradient 232 followed by a phase encoding gradient lobe 240 and a rewinder gradient lobe 242 of opposite polarity. This axial phase encoding gradient 240 is stepped through values during the scan to sample from each of the 2D k-space slices 234, 236 and 238. It should be apparent that any number of 2D k-space slices may be sampled with this pulse sequence by applying a corresponding number of different axial phase encodings.

Two in-plane readout gradients 224 and 226 are played out during the acquisition of an NMR echo signal 228 to sample k-space in a 2D plane 234, 236 or 238 along a radial trajectory. These in-plane gradients 224 and 226 are perpendicular to the axial gradient and they are perpendicular to each other. During a scan they are stepped through a series of values to rotate the view angle of the radial sampling trajectory. Each of the in-plane readout gradients is preceded by a prephasing gradient lobe 220 and 222 and followed by a rewinder gradient lobe 224 and 226. For each axial phase encoding 240, a complete set of radial projection views are acquired to sample the 2D k-space slice. As will be described below, the present invention enables these 2D k-space slices to be sampled with fewer radial projection views, which results in a shorter scan time.

It should be apparent to those skilled in the art that sampling trajectories other than the preferred straight line trajectory extending from one point on the k-space peripheral boundary, through the center of k-space to an opposite point on the k-space peripheral boundary may be used. As mentioned above, one variation is to acquire a partial NMR echo signal 228 which samples along a trajectory that does not extend across the entire extent of the sampled k-space volume. Another variation which is equivalent to the straight line projection reconstruction pulse sequence is to sample along a curved path rather than a straight line. Such pulse sequences are described, for example, in "Fast Three Dimensional Sodium Imaging", MRM, 37:706-715,1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia. It should also be apparent that the present invention may be employed with 2D as well as 3D versions of these sampling methods and references herein to the term "pixel" as used hereinafter is intended to refer to a location in either a 2D or a 3D image.

The present invention is an improved method for reconstructing images from acquired k-space projections. The method requires the reconstruction of a composite image of the FOV and the manner in which this composite image is acquired and the manner in which it is used will depend on the particular clinical application. Different preferred embodiments of the invention will now be described.

Referring particularly to FIG. 7, a first preferred embodiment is applicable to clinical situations in which a time-resolved series of images is required on a near real-time basis. This may be used, for example, in an interventional MR procedure. The first step in the procedure is to acquire and reconstruct a composite image of the subject throughout the prescribed field of view (FOV) as indicated at process block 300. This image may be acquired with any MR pulse sequence, but typically it employs the same projection reconstruction pulse sequence used to acquire the time resolved images, which in this embodiment is the pulse sequence described above and shown in FIG. 6A. However, because time resolution is not a concern, many projection views will be acquired, and preferably, enough data is acquired to satisfy the Nyquist criteria and produce an image of the desired resolution without significant streak artifacts.

If the subject of the examination moves in response to subject respiration or the cardiac cycle, the acquisition of the composite image may be gated as indicated at 302. The gating may be triggered by a respiratory gating signal or cardiac gating signal or both, depending on the subject being examined. The composite image is reconstructed from the acquired k-space data using a conventional reconstruction method. The reconstructed composite image indicates the magnitude of the NMR signal at each image pixel throughout the 2d or 3D FOV. The composite image may also be filtered by setting to zero all pixels or voxels that do not exceed a minimum threshold magnitude. Such a threshold filter darkens the background in the composite image as well as the background in the time-resolved images subsequently reconstructed using the composite image as described below. The composite image provides a priori information about the subject of the scan.

After the composite image is acquired and reconstructed, the system enters a loop in which a series of frame images are acquired and reconstructed in near real-time. More specifically, a set of image frame projections are acquired as indicated at process block 304 using the pulse sequence of FIG. 6A. This acquisition may be as few as 2-20 projection views for a 2D acquisition and as few as 250 to 500 views for a 3D acquisition. As a result, it is completed very quickly. If gating was used during acquisition of the composite image, then the same gating is used to acquire the frame image as indicated at 306. To minimize streak artifacts in the frame image the acquired N projection views should be angularly spaced as described above to uniformly sample k-space.

After the image frame projections are acquired they are motion compensated as indicated at process block 308. The composite image serves as a reference position of the subject and phase corrections are made to the image frame projections to effectively register the subject depicted therein with the reference position depicted in the composite image. A number of methods are known in the art for registering two images and in the preferred embodiment the method described in the PhD thesis of Oliver Wieben published by the University of Wisconsin in 2002 and entitled "Novel Acquisition Strategies For Time Resolved 3D, Magnetic Resonance Angiography" is employed.

Figure 4:
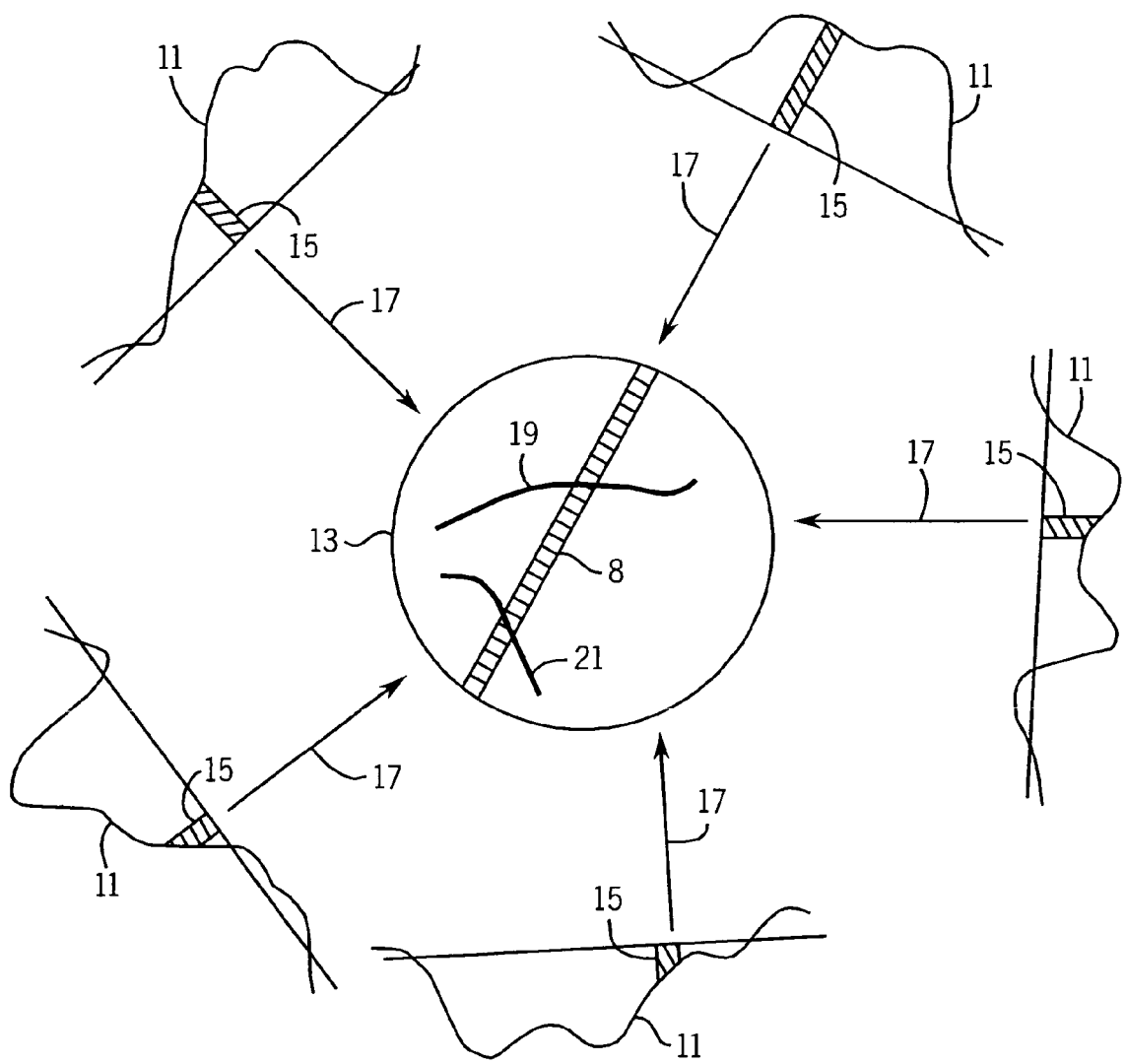
FIG. 4 is a pictorial representation of the same step as implemented according to the present invention.
Figure 5:
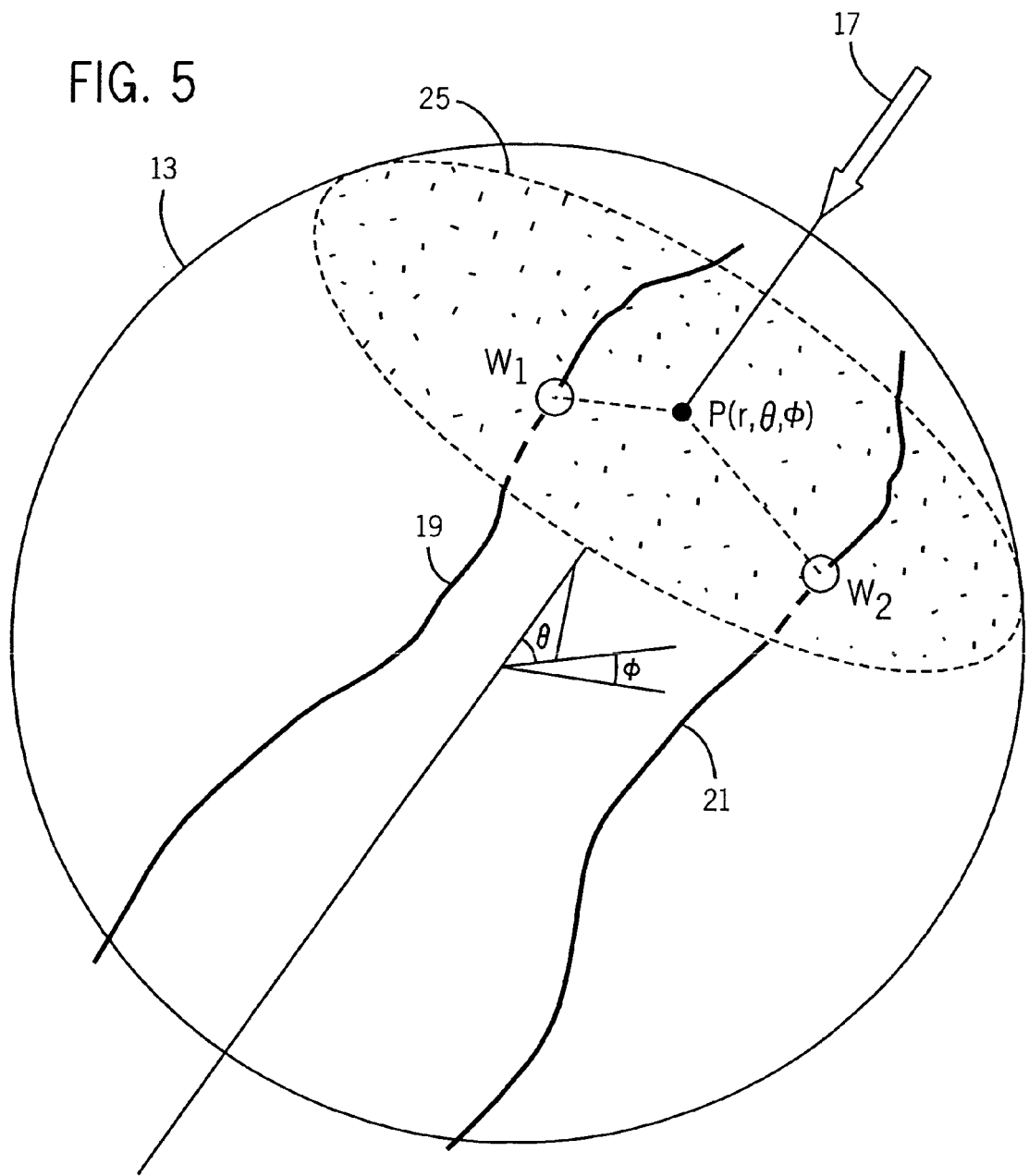
FIG. 5 is a pictorial representation of a 3D embodiment of the backprojection step according to the present invention.

As indicated by process block 310, the next step is to transform the frame image k-space projections to radon space by Fourier transforming them. The result is a set of signal profiles 11 as depicted in FIG. 4. As indicated at process block 312 in FIG. 7, each of these signal profiles is then backprojected into the VOA as depicted by path 8 in FIG. 4. This backprojection is weighted by the composite image as described above with reference to equation (2A). That is, the backprojection value (P) at any pixel (x,y,z) is normalized $(P/P_c)$ as described above and weighted by the magnitude $(C_{(x,y,z)})$ of the same pixel in the previously reconstructed composite image.

As indicated at process block 314, the backprojected signal values are then added to a frame image that is being reconstructed. The system then loops back at decision block 316 to backproject the next signal profile 11 as indicated at process blocks 318 and 312. The signal values of all the backprojected signal profiles 11 are added to the frame image and then the completed frame image is displayed as indicated at process block 320.

As indicated at process block 324, additional image frames are acquired, reconstructed and displayed in the same fashion until the process is terminated as indicated at decision block 322. However, a different set of projection views may be acquired for each image frame. The projection views acquired for successive frame images are thus interleaved in k-space. Equations 5-7 are used to produce the gradient fields needed to acquire the interleaved projections in the preferred embodiment.

The acquisition of interleaved projection views enables a variation in the image reconstruction method to be performed in which peripheral k-space data is shared between successive image frames. This view sharing concept is described in the above-cited U.S. Pat. No. 6,487,435 in the context of a conventional image reconstruction. This imaging method is employed with the present invention using the pulse sequence of FIG. 6B in which k-space data is acquired from a central region A and two peripheral regions B and C as shown in FIG. 6C. In the preferred embodiment 10 to 30 $k_z$ phase encodings are employed in each region A, B and C such that a corresponding number of slices may be reconstructed for each region.

Figure 8A:
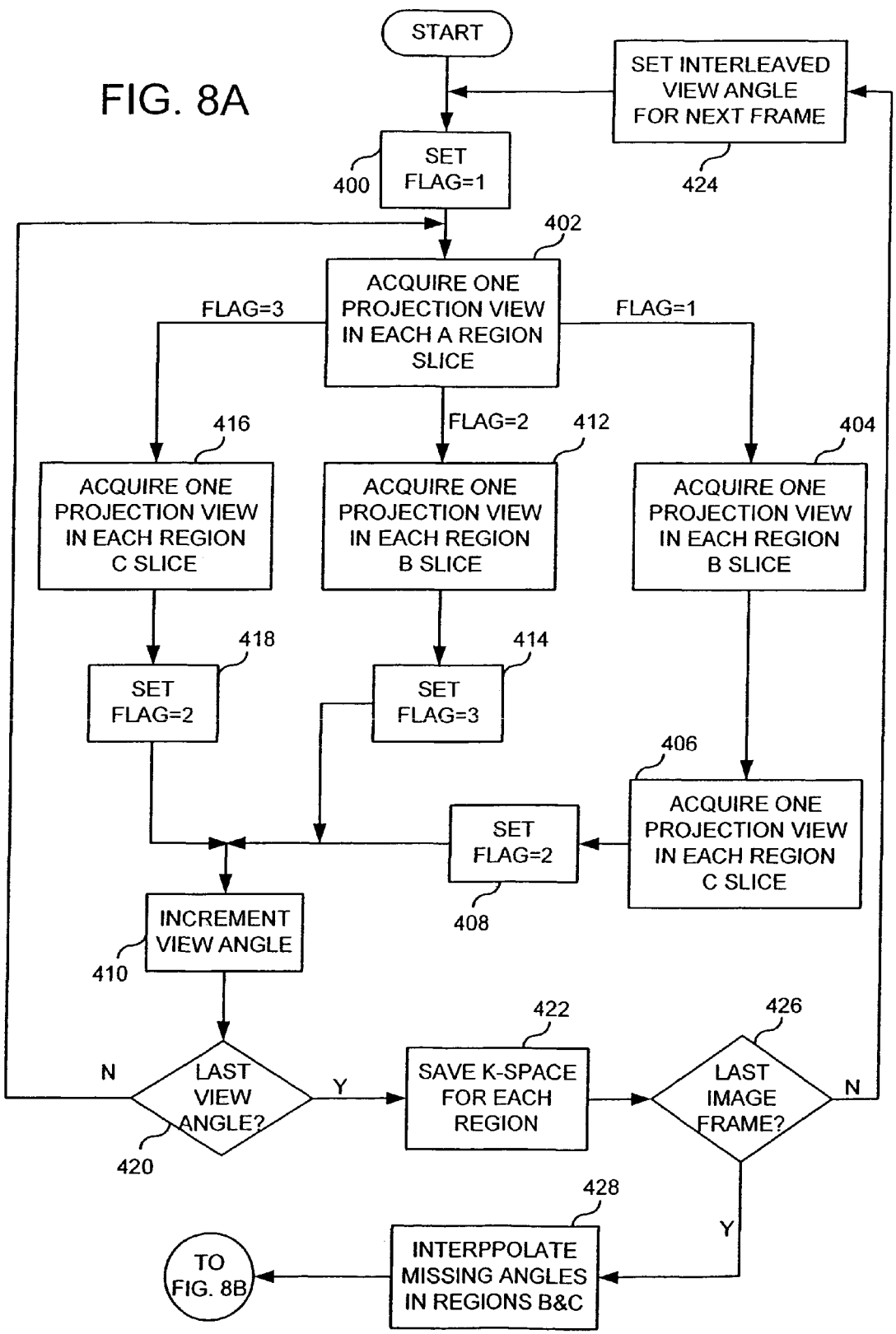
FIGS. 8A and 8B are a flow chart of another preferred method for employing the present invention in an acquisition that employs a TRICKS view sharing method.

Referring particularly to FIG. 8A, a scan is conducted to acquire a series of under sampled image frames with the projection view angles interleaved such that composite images can be formed by combining data from a plurality of acquired image frames. A loop is entered in which a flag is set to "1" as indicated at process block 400 to indicate that a new image frame is being acquired. As indicated at process block 402, the pulse sequence of FIG. 6B is then performed to acquire one projection view angle θ at each $k_z$ phase encoding in the central region A. The system then branches in one of three ways depending on the flag. With the flag set to "1" the system acquires one projection view angle θ at each $k_z$ phase encoding in region B as indicated at process block 404, and it acquires one projection view angle θ at each $k_z$ phase encoding in region C as indicated at process block 406. The flag is then set to "2" at 408 and the projection view angle θ is incremented at 410 to acquire the next projection angle. The system then loops back to process block 402 to acquire the new projection view angle θ, in the central region A.

Because the flag is now set to "2" only the region B is sampled at this view angle θ as indicated at process block 412 and the flag is set to "3" at 414. The view angle θ is then incremented again at process block 410 and the system loops back again to require k-space data from region A at process block 402. Because the flag is now set to "3", this time projection views at the new view angle θ are acquired from region C as indicated at process block 416 and the flag is set back to "2" at process block 418.

It should be apparent that as successive view angles are acquired the flag is toggled between "2" and "3" with the result that k-space data is sampled in the pattern illustrated in FIG. 9. When the last view angle $θ_n$ has been acquired as determined at decision block 420, one image frame has been acquired and the region A, B and C k-space data is saved as indicated at process block 422. In the preferred embodiment 15 equally spaced projection view angles θ are acquired during each image frame acquisition.

Referring still to FIG. 8A, the scan continues in the same manner to acquire a succession of image frames. As indicated at process block 414, however, the same projection view angles are not acquired, but instead, are interleaved with those already acquired. Thus, after two image frames are acquired 2×15=30 different projection view angles have been sampled in each region A, B and C, after three image frames have been acquired 45 different projection view angles have been samples, and so on until 15×n different, interleaved projection angles have been acquired at the end of the scan as determined at decision block 426.

It should be apparent that the scan is shortened considerably by two factors. First, only 15 projection views are acquired for each of the image frames, rather than the usual 400 to 800 views normally used to avoid image artifacts. In addition, while the central region A of k-space is sampled at every view angle θ, the peripheral regions B and C are only sampled at every other projection view angle θ as shown in FIG. 9. This reduces scan time by approximately one third, but it also means that k-space data is missing. As indicated at process block 428 in FIG. 8A, this is resolved by interpolating k-space data for the missing projection view angles. This is illustrated for one view angle $θ_2$ in FIG. 9, where interpolated data $C_2$ is produced by linearly interpolating between corresponding k-space sample points in the adjacent projection views $C_1$ and $C_3$. As a result, complete, but highly undersampled image frame k-space data sets are produced as illustrated in FIG. 10.

Figure 8B:
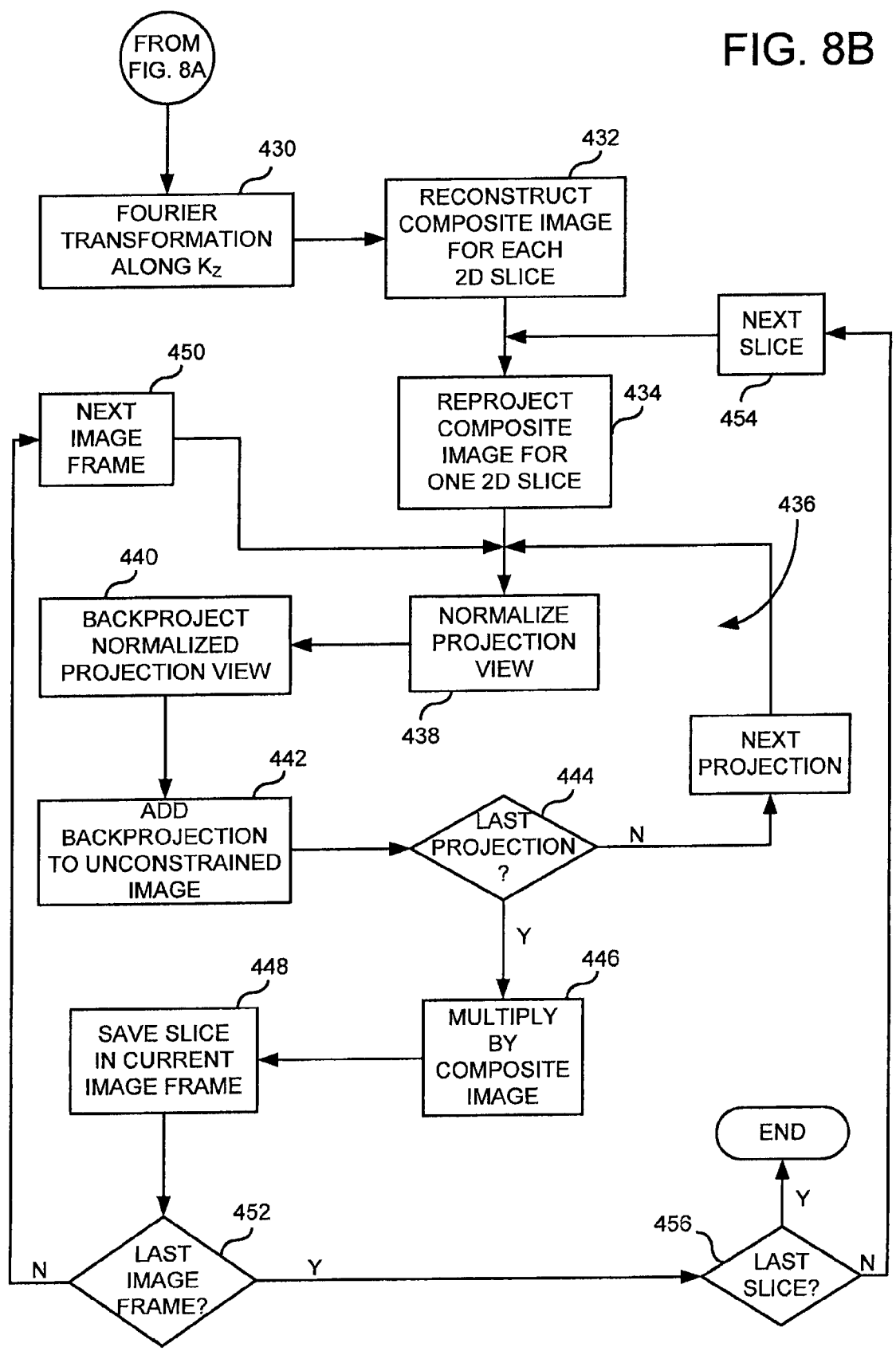

Referring to FIGS. 8B and 10, the next step is to perform a one-dimensional inverse Fourier transformation along the $k_z$ axis as indicated at process block 430. This transformation resolves signal positions along the z axis to define a plurality of 2D slices disposed along the z axis.

A composite image is then reconstructed for each 2D slice as indicated at process block 432. Preferably, all of the projection views from all of the acquired image frames are used to reconstruct each 2D composite image in order to produce the best image possible, although less than all the image frames may be used. For example, if ten image frames are acquired a total of 10×15=150 interleaved projection views may be employed in the reconstruction of each 2D composite image. A conventional image reconstruction of each 2D slice is performed and in the preferred embodiment this is done by regridding the projection view k-space samples to a 2D Cartesian grid and performing the usual two-dimensional Fourier transformation along each axis.

There are a number of alternative composite image reconstruction methods possible. Rather than producing a 2D composite image for each 2D slice, a single 3D composite image may be reconstructed for the entire volume, or separate 3D composite images may be reconstructed for each region A, B and C.

Referring particularly to FIG. 8B, each 2D slice in each acquired image frame is now reconstructed using a method taught by the present invention. As will become apparent from the description below, one 2D slice image is reconstructed for each image frame and the process is then repeated for each of the 2D slices until the image frames are completely reconstructed. The result is a 3D image for each acquired image frame.

Figure 11:
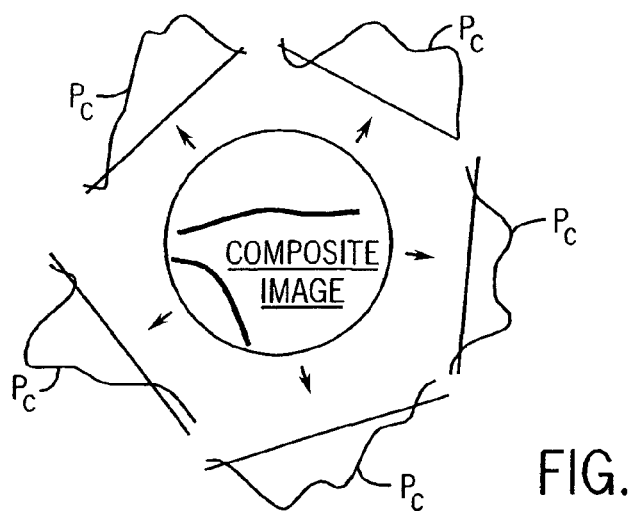
FIG. 11 is a pictorial representation of a reprojection of a composite image used in the method of FIGS. 8A and 8B.

The next step in this reconstruction process is to reproject the composite image for the current 2D slice as indicated at process block 434 and illustrated in FIG. 11. This is a conventional Radon transformation as described, for example in "Computed Tomography Principles, Design, Artifacts and Recent Advances", Jiang Hsieh, SPIE Press 2003, Chapter 3, and a composite image projection $P_c$ is produced for each view angle θ acquired during the scan. A loop is then entered in which one 2D slice in one frame image is reconstructed as indicated generally at 436.

As indicated at process block 438, the first step in the 2D slice reconstruction is to normalize an acquired projection view P of the 2D slice. This is accomplished by first performing a Fourier transformation of the k-space projection view to Radon space and then dividing the values therein by the corresponding values in the composite image projection $P_c$ at the same view angle θ. The resulting normalized projection view $P/P_c$ is then backprojected in the FOV as indicated at process block 440. The resulting backprojected values are added to an unconstrained image that is formed by summing all of the backprojected, normalized projection views in the current frame image slice as indicated at 442. This process is repeated for each of the acquired projection views (15 in this embodiment) as determined at decision block 444 and the resulting 2D unconstrained slice image that is formed is then multiplied by the corresponding composite image 2D slice as indicated at process block 446. This is a matrix multiplication in which the pixel values in the unconstrained image array are multiplied by the corresponding pixel values in the composite image array. The resulting reconstructed slice image is stored as part of the current image frame as indicated at process block 448.

The above process 436 is repeated for the same slice in the next image frame as indicated at process block 450. When the current slice has been reconstructed for each of the acquired image frames as determined at decision block 452, the next slice is reconstructed for each image frame as indicated at process block 454. The reconstruction process is completed as detected at decision block 456 when the last 2D slice of each image frame is reconstructed.

The constrained reconstruction of each highly undersampled image frame using the more fully sampled composite images results in fewer image artifacts while preserving the shorter scan time for each image frame.

Another clinical application of the present invention is contrast enhanced magnetic resonance angiography (CEMRA). In a dynamic CEMRA study image frames are acquired at a high temporal rate in order to see the inflow of contrast into the vasculature of interest. As a result, vessel brightness will be enhanced at different times during the study and the composite image used to reconstruct successive frame images according to the teachings of the present invention will not remain constant. In other words, the composite image used to reconstruct a frame image should be updated during the dynamic study to properly reflect the fact that vessels are progressively filling with contrast agent and becoming brighter in the acquired images.

Figure 12:
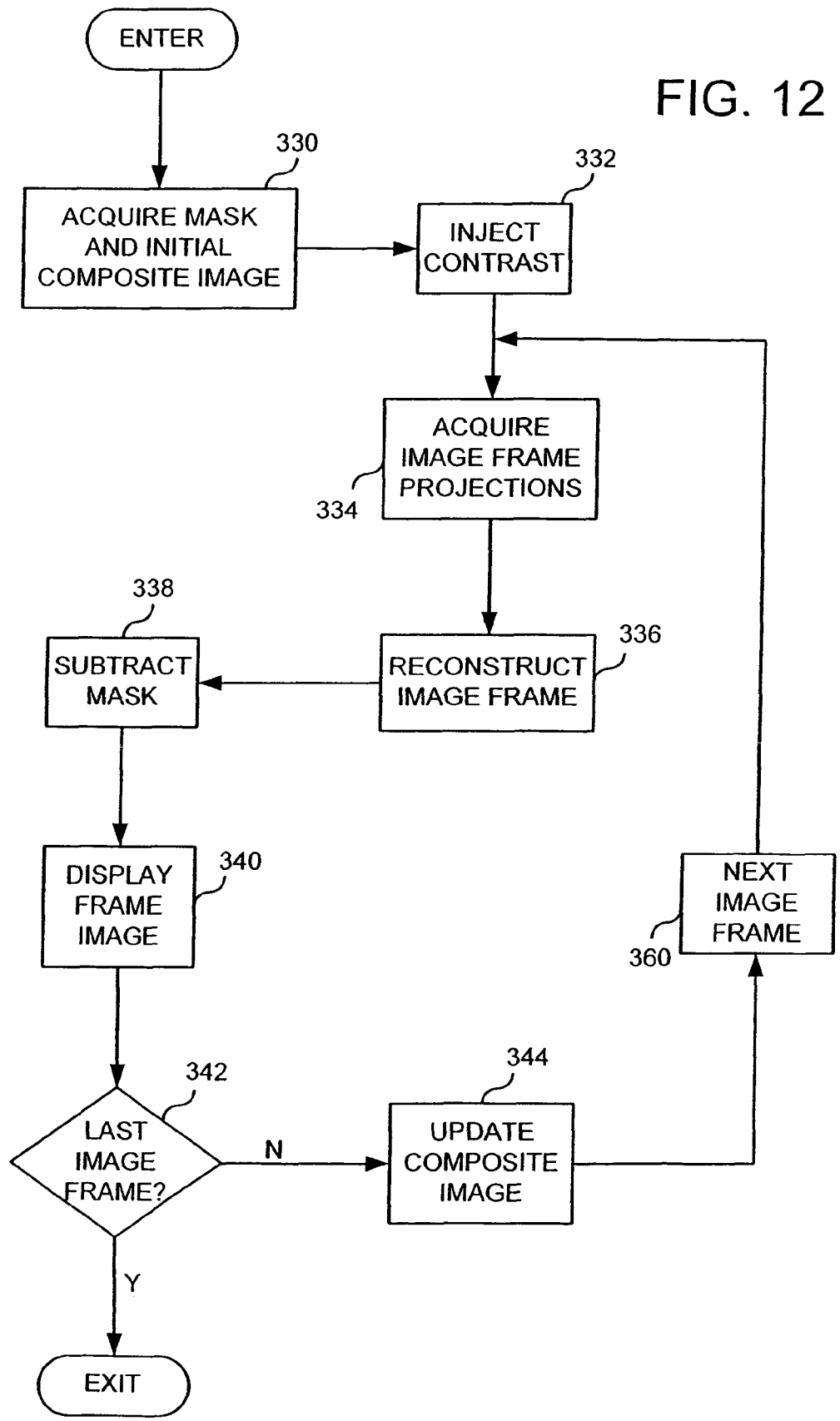
FIG. 12 is a flow chart of a preferred method for employing the present invention in a CEMRA imaging application.

Referring particularly to FIG. 12, the first step in the preferred CEMRA procedure is to acquire a pre-contrast mask image and an initial composite image as indicated at process block 330. The imaging pulse sequence of FIG. 6A is employed and sufficient views are acquired for the mask image to satisfy the Nyquist criteria. The contrast is then injected into the subject as indicated at process block 332 and a loop is entered in which frame images are acquired as rapidly as possible. It can be appreciated that the mask can be acquired after contrast administration if it is acquired before the contrast agent flows into the FOV.

As indicated at process block 334 the k-space projection views for one frame image are acquired and the frame image is reconstructed as indicated at process block 336. As in the embodiments described above, the projection views for one frame image are chosen to sample k-space as uniformly as possible and the number of views acquired is determined by the prescribed temporal resolution. The advantage of the present invention, of course, is that the number of views can be reduced to achieve higher temporal resolution without the loss of image resolution and without an increase in streak artifacts. The image frame reconstruction 336 is identical to that described above with reference to process blocks 310, 312 and 314 in FIG. 7 in which the a priori information in the composite image is employed to highly constrain the backprojection.

After the image frame is reconstructed the pre-contrast mask image is subtracted from it as indicated at process block 338. This is done to remove non-vascular tissues from the resulting frame image which is then displayed as indicated at process block 340.

Figure 13:
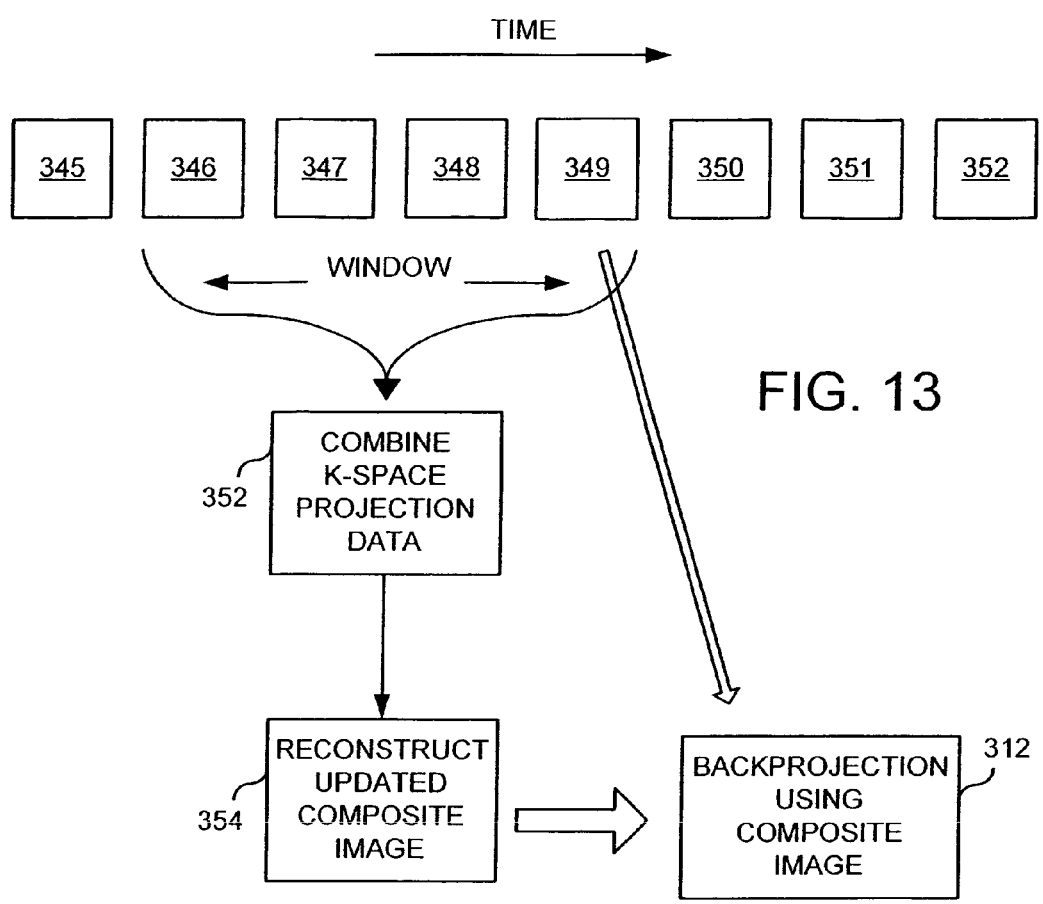
FIG. 13 is a pictorial representation of the composite image update procedure used in the CEMRA method of FIG. 12.

If additional frame images are to be acquired as determined at decision block 342 the composite image is updated first as indicated at process block 344. As indicated above, the subject vasculature being imaged is continuously changing during the dynamic study and the objective is to maintain the composite image as up-to-date as possible so that a more accurate highly constrained backprojection of the next image frame is achieved. This composite updating step is illustrated in FIG. 13 where the blocks 345-352 indicate the successive image frame acquisitions that occur during the dynamic study. If the next image frame to be reconstructed is indicated by block 349, for example, an updated composite image is formed by combining the n=3 previously acquired image frames with the current image frame. More specifically, the interleaved k-space projection views for the n previous image frames plus the current image frame are combined to form a single k-space image as indicated at process block 352. The updated composite image is reconstructed from this combined data set as indicated at process block 354. As indicated above, this is a conventional image reconstruction process. During the subsequent backprojection of image frame 349 as described above with reference to process block 312, the updated composite image is employed.

Referring still to FIG. 13, the updated composite image is thus formed by a window of n previously acquired image frames and the current image frame which most accurately reflect the current state of the subject being examined. When changes occur relatively slowly in the subject, the value of n can be increased to include more previously acquired image frames. The resulting larger number of projection views improves the quality of the resulting updated composite image. On the other hand, when changes occur quickly, n may be reduced to as few as n=1 image frames in order to properly reflect the true state of the subject being imaged. There is thus a trade-off between high SNR on the one hand and more accurate depiction of dynamic changes on the other hand that results from the selection of n.

If the frame images are reconstructed after the dynamic scan is completed, the window of acquired image frames used to update the composite image may extend to include image frames acquired after the current image frame. For example, the image frame being reconstructed may be centered in the window with a substantially equal number of other image frames acquired before and after the current image frame. Or, the current image frame may be acquired at the beginning of the window. In this post-processing of the acquired image frames a number of different image frames can be reconstructed in which both the window size and the positioning of the window relative to the current image frame may be varied to achieve the best results.

Referring again to FIG. 12, after the composite image is updated, the system loops back to acquire the next frame image as indicated at process block 360. Because the updated composite image is formed by combining previously acquired image frames, the projection views from one frame to the next should be interleaved as discussed above such that k-space is sampled substantially uniformly when k-space data from n successive image frames are combined.

Figure 14:
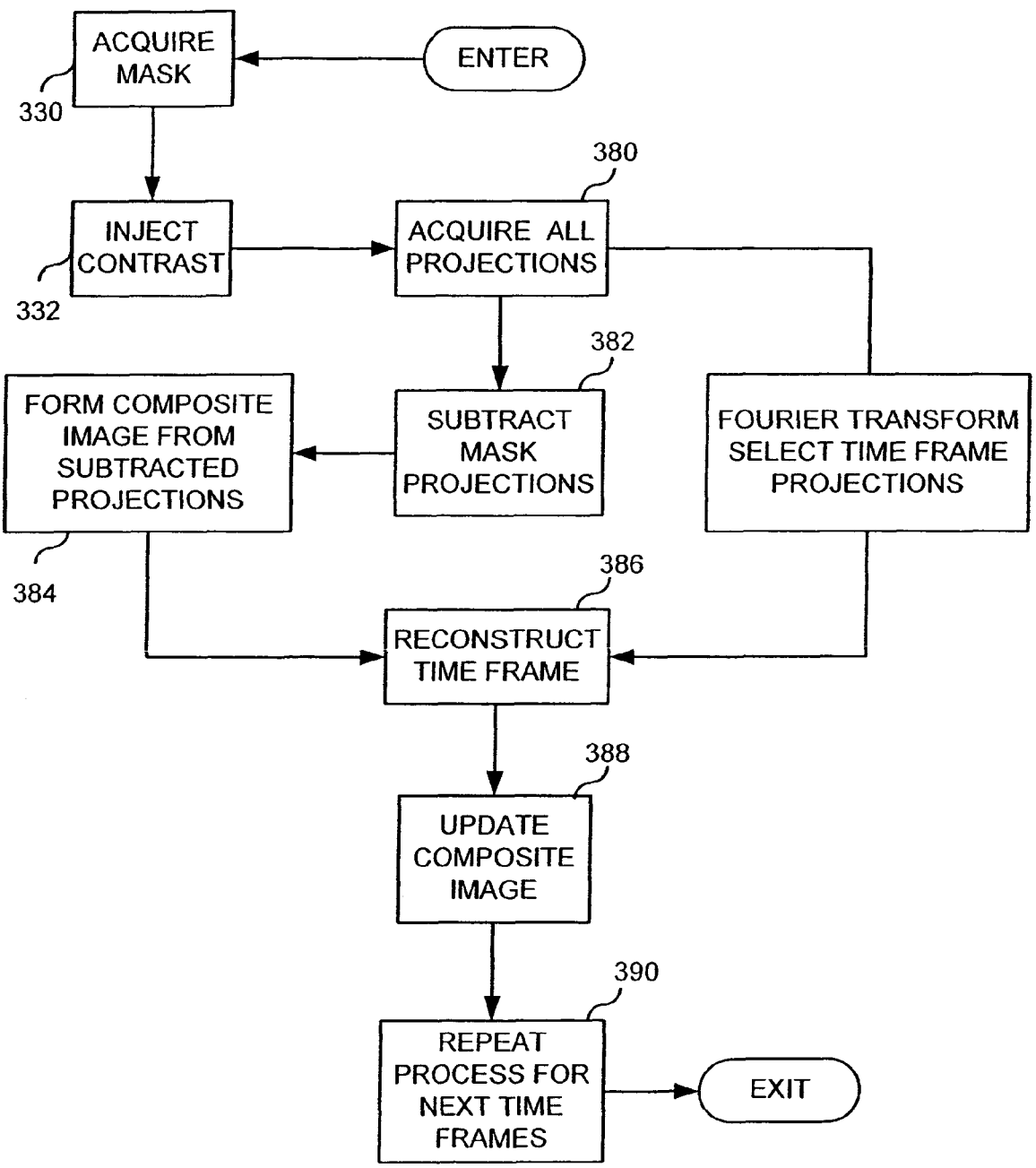
FIG. 14 is a flow chart of yet another method for employing the present invention in a CEMRA imaging application.

In the CEMRA method depicted in FIG. 12 and described above the image frames are reconstructed and displayed in near real-time as the dynamic study is performed. An alternative CEMRA method is depicted in FIG. 14 in which all the image frames are acquired at process block 380 before image reconstruction is performed. In this embodiment the mask projections acquired previously at process block 330 before contrast is injected at process block 332 are subtracted from corresponding post-injection k-space projections as indicated at process block 382. A substantial number of the subtracted projections may be used to reconstruct a composite image as indicated at process block 384. A standard image reconstruction method is used because there is a more complete set of radial projections available from the study. However, to keep the composite image up to date with the image frame to be constructed at process block 386, only subtracted projections acquired contemporaneously with the selected time frame are typically used to form the composite image as depicted in FIG. 13. The image frame is reconstructed at process block 386 by Fourier transforming the selected acquired projection views to Radon space and performing a highly constrained backprojection using the composite image as described above.

As indicated at process blocks 388 and 390, additional image frames can be reconstructed by updating the composite image produced from subtracted projections and repeating the backprojection with the properly selected projections.

An advantage of this embodiment of the invention is that the mask image data is subtracted from the acquired image data before the highly constrained backprojection is performed. This removes from the FOV many structures which are of no clinical value and results in a "sparse" data set that enables the backprojection process to be more accurately focused on the structures of clinical interest. Also, because all the data is acquired before image reconstruction begins, the composite image can be updated with a window of projection views acquired both before and after the acquisition of the current image frame. This allows more projection views to be combined.

Whereas the objective in the embodiments described above is to employ a composite image which depicts the subject being imaged as accurately as possible, there are clinical situations in which it is advantageous to deliberately alter the composite image. One such situation, for example, is when conducting a CEMRA study of the renal arteries where the aorta appears in the field of view. The dominant NMR signal from the aorta can produce streak artifacts that are difficult to remove. In this instance it is desirable to suppress this signal since it is of no clinical value. This can be achieved with the present invention by altering the composite image used for backprojecting the frame images.

An embodiment of the invention in which such an alteration of the composite image is made to filter out objects in the field of view is illustrated in FIG. 15. This embodiment is a post processing method that enhances the quality of previously acquired under-sampled and time-resolved image frames. More specifically, the scan includes the acquisition of a series of image frame projections during a study of a subject as indicated by process block 364. This acquired k-space projection data are stored and processed after the scan is completed.

The first post processing step as indicated by process block 366 is to reconstruct one or more composite images by combining interleaved k-space projection views from a plurality of the acquired image frame projection sets. This is a conventional image reconstruction and the resulting composite image is then displayed as indicated at process block 367. An operator edits the composite image as indicated at process block 368. In the example clinical application described above, the operator would encircle the pixels that depict the aorta and set their values to zero. In other words, the aorta is removed from the composite image. To further suppress the unwanted object, the encircled pixels to be deleted may also be Fourier transformed back to k-space and subtracted from the corresponding k-space projections for each image frame.

The image frames are then reconstructed using this altered composite image and the altered k-space projections. As indicated as process block 370, one set of image frame k-space projections are Fourier transformed to Radon space and backprojected using the edited composite image and the constrained backprojection method of the present invention to produce a frame image which is displayed as indicated at process block 372. This step is identical to the reconstruction described above with reference to the process blocks 310, 312 and 314 in FIG. 7 and it is repeated for all the acquired image frames as determined at decision block 374. It should be apparent that to accommodate sudden changes that occur in the subject during the study more than one composite image may be created and used to reconstruct frame images in the series as described above. In such case, each updated composite image is edited to remove the object of concern before it is used in the backprojection step.

Yet another embodiment of the invention produces phase contrast MRA images. In this embodiment the pulse sequence that is used employs an additional motion encoding gradient as described, for example in U.S. Pat. No. 6,188,922 entitled "Phase Contrast Imaging Using Interleaved Projection Data" and a contrast agent is usually not employed. The phase images that are reconstructed use the backprojection method described above with a composite image formed with contemporaneously acquired projections.

The invention claimed is:

1. A method for producing an image of a subject positioned in the field of view (FOV) of a magnetic resonance imaging (MRI) system, the steps comprising:
   a) acquiring with the MRI system a set of projection views of the subject positioned in the FOV;
   b) producing a composite image with the MRI system which indicates a value at each composite image pixel of the subject positioned in the FOV; and
   c) reconstructing an image of the subject by:
      c)i) backprojecting each projection view in the set into the FOV and weighting the value backprojected into each image pixel by the value of the corresponding pixel in the composite image; and
      c)ii) summing the backprojected values for each image pixel.

2. The method as recited in claim 1 in which each image pixel backprojected value $S_n$ is calculated in step c)i) as $$S_n = (P \times C_n) \bigg/ \sum_{n=1}^{N} C_n$$

where: P=the projection view value being backprojected;
   $C_n$=corresponding pixel value in the composite image;
   $S_n$=the value of the $n^{th}$ pixel along the backprojection path; and
   N=total number of pixels along the backprojection path.

3. The method as recited in claim 1 in which step b) includes editing the composite image to remove an object therein and to thereby substantially minimize the appearance of that object in the reconstructed image.

4. The method as recited in claim 1 in which the weighting in step c)i) includes normalizing each projection view using a corresponding projection view from the composite image and multiplying the backprojected value by the value of the corresponding pixel in the composite image.

5. The method as recited in claim 4 which further includes:
   d) periodically updating the composite image during the reconstruction of the series of images to depict therein changes that occur in the subject during the examination.

6. The method as recited in claim 5 in which the updating of the composite image includes reconstructing the composite image using projection views acquired in step a).

7. The method as recited in claim 1 in which step a) includes acquiring k-space projection views of the subject and step c) includes Fourier transforming the k-space projection views.

8. The method as recited in claim 1 in which step a) is performed in response to a gating signal indicative of a selected physiological event in the subject.

9. The method as recited in claim 1 in which the FOV is three-dimensional, a three-dimensional image is produced, and the image $I_{(x,y,z)}$ reconstructed in step c) is:

$$I(x, y, z) = \sum (P(r, \theta, \phi) * C(x, y, z)_{(r,\theta,\phi)} / P_c(r, \theta, \phi))$$

where the summation ($\Sigma$) is over all projection views in the acquired set;

$I_{(x,y,z)}$ is the image value at FOV pixel location x,y,z; $P_{(r,\theta,\phi)}$ is the back projected value from the view acquired at a view angle $\theta$, $\phi$; $C_{(x,y,z)}$ is the composite image value at the pixel location x,y,z; and $P_c(r,\theta,\phi)$ is the profile value projected from the composite image at the view angle $\theta$, $\phi$.

10. The method as recited in claim 1 which includes:
    d) acquiring a mask image that depicts at each of its image pixels the subject positioned in the FOV prior to the administration of a contrast agent;
    e) administering a contrast agent to the subject prior to performing steps a) and b); and
    f) subtracting the mask image from the composite image prior to performing step c).

11. The method as recited in claim 10 in which both the mask image and the composite image are acquired as sets of projection views and step f) is performed by subtracting projection views in the mask image set from corresponding projection views in the composite image set.

12. The method as recited in claim 10 in which step f) is performed by subtracting pixels in the mask image from corresponding pixels in the composite image.

13. The method as recited in claim 1 in which step c) includes Fourier transformation each projection view before performing step c)i).

14. The method as recited in claim 1 which includes:
    d) reprojecting the composite image at view angles used to perform step a); and
    in which the weighting in step c)i) includes normalizing each projection view by dividing values therein by corresponding values in the projection view of the composite image at the same view angle.

15. A method for producing a series of image frames of a subject positioned in the field of view (FOV) of a magnetic resonance imaging (MRI) system, the steps comprising:
    a) acquiring a series of image frame k-space data sets, each image frame k-space data set including k-space samples from a central region of k-space and k-space samples from a plurality of peripheral k-space regions, and in which the k-space samples in each image frame k-space data set are interleaved with the k-space samples in other image frame k-space data sets;
    b) reconstructing a central region composite image from central region k-space samples from a plurality of said image frame k-space data sets;
    c) reconstructing a first peripheral region composite image from k-space samples from one of said peripheral k-space regions in a plurality of said image frame k-space data sets;
    d) reconstructing a second peripheral region composite image from k-space samples from another one of said peripheral k-space regions in a plurality of said image frame k-space data sets; and
    e) reconstructing each of the series of image frames from its corresponding k-space data set using a priori information in the composite images from steps b), c) and d) to weight the pixel values in the image frame.

16. The method as recited in claim 15 in which the k-space samples are acquired as projection views and step e) includes:
    e)i) Fourier transforming the projection views in an image frame k-space data set; and
    e)ii) backprojecting each Fourier transformed projection view into the FOV and weighting the value backprojected into each image frame pixel by the value of the corresponding pixel in one of the composite images.

17. The method as recited in claim 16 in which the weighting in step e)ii) includes normalizing each Fourier transformed projection view using a corresponding projection view from said one composite image and multiplying the backprojected value by the value of the corresponding pixel in said one composite image.

18. The method as recited in claim 15 in which each region of k-space includes a plurality of two-dimensional slices and each region composite image includes a corresponding plurality of two-dimensional composite images.

19. A method for producing a series of image frames of a subject positioned in the field of view (FOV) of a magnetic resonance imaging (MRI) system, the steps comprising:
    a) acquiring a series of incomplete image frame k-space data sets, each image frame k-space data set including k-space samples from a central region of k-space and k-space samples from a plurality of peripheral k-space regions, and in which the k-space samples in each image frame k-space data set are interleaved with the k-space samples in other image frame k-space data sets;
    b) producing a series of corresponding complete image frame k-space data sets by calculating peripheral region k-space data from acquired peripheral region k-space data;
    c) reconstructing a composite image from k-space samples from a plurality of said complete image frame k-space data sets;
    d) reconstructing each of the series of image frames from its corresponding complete image frame k-space data set using a priori information in the composite image to weight the pixel values in the image frame.

20. The method as recited in claim 19 in which the k-space samples are acquired as projection views and step d) includes:
    d)i) Fourier transforming the projection views in a complete image frame k-space data set; and
    d)ii) backprojecting each Fourier transformed projection view into the FOV and weighting the value backprojected into each image frame pixel by the value of the corresponding pixel in the composite image.

21. The method as recited in claim 20 in which the weighting in step d)ii) includes normalizing each Fourier transformed projection view using a corresponding projection view from said composite image and multiplying the backprojected value by the value of the corresponding pixel in said composite image.

* * * * *